(12) United States Patent
Boyce

(10) Patent No.: US 8,299,097 B2
(45) Date of Patent: Oct. 30, 2012

(54) METHODS FOR TREATING INFLAMMATORY DISORDERS

(75) Inventor: Joshua A. Boyce, Sherborn, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 535 days.

(21) Appl. No.: 12/557,024

(22) Filed: Sep. 10, 2009

(65) Prior Publication Data

US 2010/0081684 A1    Apr. 1, 2010

Related U.S. Application Data

(60) Provisional application No. 61/096,640, filed on Sep. 12, 2008.

(51) Int. Cl.
*A61K 31/445* (2006.01)
(52) U.S. Cl. .................................................. 514/326
(58) Field of Classification Search ................... 514/326
See application file for complete search history.

(56) References Cited

U.S. PATENT DOCUMENTS

| 4,529,596 A | 7/1985 | Aubert et al. |
| 4,847,265 A | 7/1989 | Badorc et al. |
| 2008/0108635 A1 | 5/2008 | Zhang et al. |

FOREIGN PATENT DOCUMENTS

WO    2005/076007    8/2005

OTHER PUBLICATIONS

Kowal et al., Clinical and Experimental Allergy, 2006;36:426-432.*
Beller et al., The Journal of Biological Chemistry, 279(44):46129-46134 (2004). "Targeted gene disruption reveals the role of the cysteinyl leukotriene 2 receptor in increased vascular permeability and in bleomycin-induced pulmonary fibrosis in mice."
Dahlen et al., Am J Respir Crit Care Med, 165:9-14 (2002). "Improvement of aspirin-intolerant asthma by montelukast, a leukotriene antagonist."
Gauvreau et al., Am J Respir Crit Care Med, 164:1495-1500 (2001). "Inhaled leukotriene E4, but not leukotriene D4, increased airway inflammatory cells in subjects with atopic asthma."
Henderson et al., Am J Respir Crit Care Med, 173:718-728 (2006). "Reversal of allergen-induced airway remodeling by CysLT1 receptor blockade."
Israel et al., JAMA, 275(12):931-936 (1996). "Effect of treatment with zileuton, a 5-lipoxygenase inhibitor, in patients with asthma."

Kim et al., J Immunol, 176:4440-4448 (2006). "Cysteinyl leukotrienes regulate Th2 cell-dependent pulmonary inflammation."
Knorr et al., JAMA, 279(15):1181-1186 (1998). "Montelukast for chronic asthma in 6- to 14-year-old children: a randomized, double-blind trial."
Lee et al., Proc Natl Acad Sci USA, 81:4922-4925 (1984). "Leukotriene E4-induced airway hyperresponsiveness of guinea pig tracheal smooth muscle to histamine and evidence for three separate sulfidopeptide leukotriene receptors."
Parachuri et al., The Journal of Biological Chemistry, 283(24):16477-16487 (2008). "Leukotriene E4 activates peroxisome proliferator-activated receptor gamma and induces prostaglandin D2 generation by human mast cells."
Christie, P.E. et al., Am Rev Respir Dis, 146:1506-1510 (1992). "Effect of indomethacin on leukotriene4-induced histamine hyperresponsiveness in asthmatic subjects."
Christie, P.E. et al., Eur Respir J, 6:1468-1473 (1993). "Airway responsiveness to leukotriene C4 (LTC4) leukotriene E4 (LTE4) and histamine in aspirin-sensitive asthmatic subjects."
Csoma, Z. et al., Am J Respir Crit Care, 166:1345-1349 (2002). "Increased leukotrienes in exhaled breath condensate in childhood asthma."
Drazen, J.M. et al., Am Rev Respir Dis, 146:104-108 (1992). "Recovery of leukotriene E4 from the urine of patients with airway obstruction."
Kirshenbaum, A.S. et al., Leukemia Res, 27:677-682 (2003). "Characterization of novel stem cell factor responsive human mast cell lines LAD 1 and 2 established from a patient with mast cell sarcoma/leukemia; activation following aggregation of Fc-epsilon-RI or Fc-gamma-RI."
Laitinen, LA. et al., Lancet, 341:989 (1993). "Leukotriene E4 and granulocytic infiltration into asthmatic airways."
Lam, S. et al., J Allergy Clin Immunol, 81:711-717 (1988). "Release of leukotrienes in patients with bronchial asthma."
Liu, M.C. et al., J Allergy Clin Immunol, 98:859-871 (1996). "Acute and chronic effects of a 5-lipoxygenase inhibitor in asthma: A 6-month randomized multicenter trial."
Wenzel, S.E. et al., Am Rev Respir Dis, 142:112-119 (1990). "Elevated levels of leukotriene C4 in bronchoalveolar lavage fluid from atopic asthmatics after endobronchial allergen challenge."

* cited by examiner

*Primary Examiner* — San-Ming Hui
(74) *Attorney, Agent, or Firm* — Nixon Peabody LLP; David S. Resnick

(57) ABSTRACT

The invention described herein is based, in part, on the discovery that thieno[3,2-c] pyridine derivatives prevent inflammation in the setting of inflammatory disorders, such as asthma. Described herein are methods for treating inflammatory disorders including, for example asthma, by administering a thieno[3,2-c] pyridine derivative compound to an individual in need thereof.

6 Claims, 28 Drawing Sheets

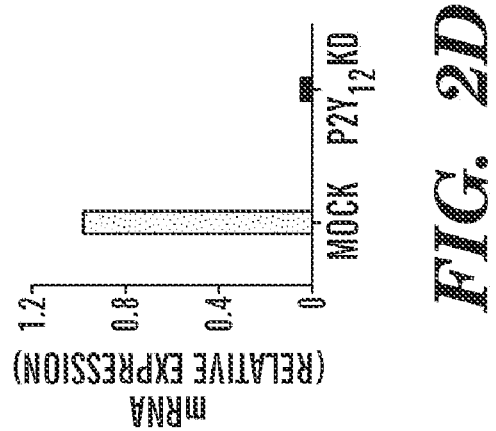
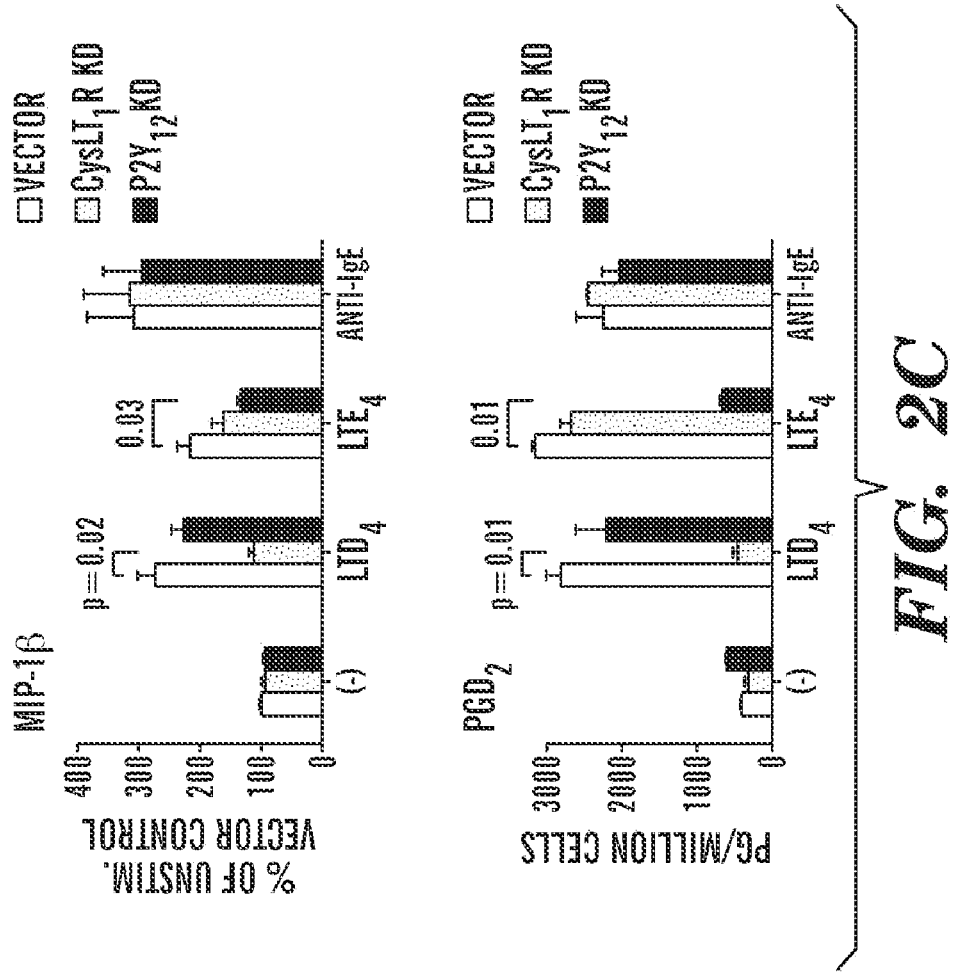
FIG. 2D
FIG. 2C

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caacaagaaa tgcaagccgt cga                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtttacttc tctgaggtta cat                                            23
```

METHODS FOR TREATING INFLAMMATORY DISORDERS

CROSS-REFERENCE TO RELATED APPLICATIONS

This application claims benefit under 35 U.S.C. §119(e) of the U.S. Provisional Application No. 61/096,640, filed Sep. 12, 2008, the content of which is incorporated herein by reference in its entirety.

GOVERNMENT SUPPORT

This invention was made with Government support under Grant No. AI53202 awarded by the National Institutes of Health. The Government has certain rights in the invention.

FIELD OF THE INVENTION

The methods described herein relate to the treatment of inflammatory disorders such as asthma.

BACKGROUND

Cysteinyl leukotrienes (cys-LTs) are lipid inflammatory mediators generated in vivo by mast cells (MCs), eosinophils, myeloid dendritic cells (DCs), basophils, and macrophages (reviewed in Kanaoka, Y., and J. A. Boyce. 2004. *J. Immunol.* 173:1503-1510). Cysteinyl leukotrienes abound in mucosal inflammation, play a validated role in human asthma (Wenzel, S. E., et al. 1990. *Am. Rev. Respir. Dis.* 142:112-119; Israel, E., et al. 1996. *JAMA* 275:931-936), and are important mediators in mouse models of pulmonary inflammation, remodeling, and fibrosis (Kim, D. C., et al. 2006. *J. Immunol.* 176:4440-4448; Beller, T. C., et al. 2004. *J. Biol. Chem.* 279:46129-46134; Henderson, W. R. Jr., et al. 2006. *Am. J. Respir. Crit. Care Med.* 173:718-728). Drugs that interfere with cys-LT synthesis (Israel, E., et al. 1996 *JAMA* 275:931-936) or that block the type 1 receptor for cys-LTs (CysLT$_1$R) (Dahlen, S. E., et al. 2002. *Am. J. Respir. Crit. Care Med.* 165:9-14) are efficacious treatments for asthma, rhinitis, and nasal polyposis. Cys-LTs are synthesized from the precursor arachidonic acid following its liberation by calcium-dependent cytosolic phospholipase $A_2$ (cPLA$_2$) from membrane phospholipids (Clark, J. D., et al. 1991 *Cell.* 65:1043-1051) and its conversion to LTA$_4$ by 5-lipoxygenase (5-LO) in concert with 5-lipoxygenase activating protein (FLAP) (Malavia, R., et al. 1993. *J. Biol. Chem.* 268:4939-4944; Dixon, R. A., et al. 1990 *Nature* 343:282-284). LTA$_4$ is conjugated to reduced glutathione by LTC$_4$ synthase (LTC$_4$S), a homotrimeric integral nuclear membrane protein (Ago, H., et al. 2007 *Nature* 448:609-612). The cys-LTs comprise three distinct ligands. LTC$_4$, the parent molecule, is exported to the extracellular space by a multidrug resistant protein after synthesis (Robbiani, D. F., et al. 2000 *Cell.* 103:757-768), where it is successively converted to LTD$_4$ by γ-glutamyl leukotrienease-mediated removal of glutamic acid (Shi, Z. Z., et al. 2001. *Molec. Cellul. Biol.* 21:5389-5395). LTD$_4$ is then converted to LTE$_4$ by dipeptidase-mediated removal of glycine (Lee, C. W., et al. 1983. *Immunology.* 48:27-35). LTC$_4$ is the only intracellular cys-LT, and LTD$_4$ is the most powerful contractile agonist. The extracellular half-life of LTD$_4$ is short (minutes) due to its rapid conversion to LTE$_4$, effectively limiting its duration of action in vivo. LTE$_4$ is stable and excreted in the urine (Sala, A., et al. 1990. *J. Biol. Chem.* 265:21771-21778). The stability of LTE$_4$ accounts for the fact that it is the dominant cys-LT detected in biologic fluids. Consequently, LTE$_4$ can be monitored in the urine (Drazen, J. M., et al. 1992. *Am. Rev. Respir. Dis.* 146:104-108), sputum (Lam, S., et al. 1988. *J. Allergy Clin. Immunol.* 81:711-717), and exhaled breath condensate (Csoma, Z., et al. 2002. *Am. J. Respir. Crit. Care.* 166:1345-1349) as an index of the cys-LT synthetic pathway activity in human disease states such as asthma.

To date, two G protein coupled receptors (GPCRs) for cys-LTs, respectively termed CysLT$_1$R and the type 2 cys-LT receptor (CysLT$_2$R) have been cloned and characterized (Lynch, K. R., et al. 1999. *Nature.* 399:789-793; Heise, C. E., et al. 2000. *J. Biol. Chem.* 275:30531-30536). These receptors share 38% amino acid identity. Each is 24-32% identical to the purinergic (P2Y) class of GPCRs that regulate cellular responses to extracellular nucleotides (Mellor, E. A., et al. 2001. *Proc. Natl. Acad. Sci. USA.* 98:7964-7969), suggesting a phylogenetic relationship between these two GPCR classes. The human CysLT$_1$R, encoded by a gene on chromosome Xq21.13, is a high-affinity receptor for LTD$_4$ (Kd~1 nM) (Lynch, K. R., et al. 1999. *Nature.* 399:789-793), whereas the human CysLT$_2$R is encoded by a gene on chromosome 13q14 and has equal affinity for LTC$_4$ and LTD$_4$ (Kd~10 nM) (Heise, C. E., et al. 2000. *J. Biol. Chem.* 275:30531-30536). Although neither receptor has significant affinity for LTE$_4$, the existence of an additional LTE$_4$-reactive receptor has long been suspected. Early studies demonstrated that purified, synthetic LTE$_4$ was more potent than LTC$_4$ or LTD$_4$ for inducing contraction of guinea pig tracheal rings (Lee, T. H., et al. 1984. *Proc. Natl. Acad. Sci. USA.* 81:4922-4925). Of the three cys-LTs, only LTE$_4$ potentiated the contractile response of guinea pig trachea to histamine, a response that could be blocked by the administration of a nonselective inhibitor of the cyclooxygenase (COX) enzymes, indomethacin. LTE$_4$ inhalation by asthmatic individuals potentiated their airway hyperresponsiveness (AHR) to subsequent challenges with either histamine or methacholine; this potentiation was blocked by oral administration of indomethacin (Christie, P. E., et al. 1992. *Am. Rev. Respir. Dis.* 146:1506-1510). Inhalation of LTE$_4$, but not of LTD$_4$, caused eosinophils, basophils, and MCs to accumulate in the bronchial mucosa of asthmatic individuals (Laitinen, L. A., et al. 1993. *Lancet.* 341:989; Gauvreau, G. M., et al. 2001. *Am. J. Respir. Crit. Care Med.* 164:1495-1500). Patients with exacerbated respiratory disease (AERD), a syndrome characterized by asthma, nasal polyposis, and marked cys-LT over-production, exhibit selectively enhanced bronchoconstriction in response to LTE$_4$ relative to LTC$_4$ or to histamine when compared to aspirin-intolerant asthmatic individuals (Christie, P. E., et al. 1993. *Eur. Respir. J.* 6:1468-1473). Thus, the potency of LTE$_4$ as an inducer of inflammatory and physiologic effects in vivo is not explained by the pharmacology of the classical GPCRs for cys-LTs, which preferentially bind the metabolic precursors of LTE4. Thus, the three cys-LTs are all potent mediators, and show considerable tissue specificity for their respective actions. Both a 5-LO inhibitor (zileuton) and drugs that block CysLT1R (Knorr, B., et al. (1998) *JAMA.* 279:1181-1186) show clinical efficacy in asthma, despite the negligible activity of LTE4 at CysLT1R, and the fact that zileuton blocks only ~50% of cys-LT generation in vivo (Israel, E., J. et al. (1996) *JAMA.* 275:931-936; Liu, M. C., et al., (1996) *J. Allergy Clin. Immunol.* 98:859-871). Identification of receptor(s) and pathways through which LTE$_4$ exerts its effects may be highly significant in terms of the pathobiology of mucosal inflammation, as well as the treatment of asthma, AERD, and related diseases in which local concentrations of LTE$_4$ are elevated and/or end-organ reactivity to LTE$_4$ is high.

MCs are powerful effector cells relevant to asthma. They respond strongly to cys-LTs and are a useful cell type for modeling cys-LT-induced signaling events and receptor functions. It has been previously demonstrated that human and mouse MCs express both CysLT$_1$R (Mellor, E. A., et al. 2001. *Proc. Natl. Acad. Sci. USA.* 98:7964-7969) and CysLT$_2$R (Mellor, E. A., et al. 2003. *Proc. Natl. Acad. Sci. USA.* 100: 11589-11593), and that these receptors constitutively form heterodimers on this cell type (Jiang, Y., et al. 2007. *Blood.* 110:3263-3270). Stimulation of MCs with LTD$_4$, the most potent agonist of the CysLT$_1$R, transactivates the Kit tyrosine kinase (Jiang, Y., et al. 2006. *J. Immunol.* 177:2755-2759), induces calcium flux (Mellor, E. A., et al. 2001. *Proc. Natl. Acad. Sci. USA.* 98:7964-7969), and phosphorylates mitogen activated protein kinase-kinase and its downstream effector, extracellular signal-regulated kinase (ERK) (Mellor, E. A., et al. 2002. *J. Exp. Med.* 195:583-592). These signaling events amplify MC proliferation (Jiang, Y., et al. 2006. *J. Immunol.* 177:2755-2759) and induce their generation of cytokines and chemokines (Mellor, E. A., et al. *J. Exp. Med.* 195:583-592). CysLT$_1$R is required for all of these LTD$_4$-induced responses, whereas CysLT$_2$R acts to inhibit them (Jiang, Y., et al. 2007. *Blood.* 110:3263-3270). It was recently reported that LTE$_4$ induces ERK activation and COX-2 expression, and causes prostaglandin D$_2$ (PGD$_2$) and macrophage inflammatory protein-1β (MIP-1β) generation by LAD2 cells, a well-differentiated human MC line (Paruchuri, S., et al. (2008) *J. Biol. Chem.* 283:16477-16487; Kirshenbaum, A. S., et al. (2003) *Leukemia Res.* 27:677-682), and to a lesser extent by primary cord blood-derived human MCs (hMCs). LTE4-mediated production of PGD2 by LAD2 cells was unaffected by short hairpin RNA (shRNA)-mediated knockdown of either CysLT1R or CysLT2R (Foster, C. J., et al. *J. Clin. Invest.* 107:1591-1598), supporting the presence of a previously unrecognized LTE4-reactive receptor on this cell type. ERK activation in response to LTE$_4$, but not to LTD$_4$, depended on indirect activation of the nuclear transcription factor peroxisome proliferator activated receptor (PPAR)-γ, which also was required for MIP-1β generation, COX-2 induction, and PGD$_2$ generation. Moreover, LTE$_4$-mediated production of PGD$_2$ was unaffected by short hairpin RNA (shRNA)-mediated knockdown of either CysLT$_1$R or CysLT$_2$R, which respectively abrogated and amplified the responses to LTD$_4$ stimulation (Paruchuri, S., et al. 2008. *J. Biol. Chem.* 283: 16477-16487). These findings implied the existence of a distinct receptor-mediated pathway for the generation of inflammatory mediators in response to LTE$_4$, occurring independently from the classical receptors.

SUMMARY OF THE INVENTION

Described herein is a method for treating inflammatory disorders including, for example asthma, by administering a thieno[3,2-c] pyridine derivative compound to an individual in need thereof.

One aspect relates to a method of treating an inflammatory disorder in a subject, the method comprising administering to a subject having an inflammatory disorder a therapeutically effective amount of a compound having the formula:

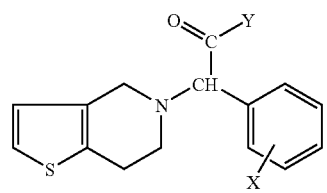

in which Y represents hydroxyl, an OR group wherein R is a straight or branched lower alkyl radical, or

in which $R_1$ and $R_2$ are each independent of each other and represents hydrogen or a straight or branched lower alkyl group; or $R_1$ and $R_2$ form together with the nitrogen atom to which they are attached a heterocycle, selected from the group consisting of pyrrolidino, pipieridino, morpholino, piperazino, N-lower alkyl piperazino; and X represents hydrogen, a halogen or a lower alkyl radical; and their addition salts with pharmaceutically acceptable mineral or organic acids if Y represents the group OR or

or with mineral bases if Y represents OH, including both enantiomeric forms or their mixture.

A mineral acid can include e.g., hydrochloric acid, nitric acid, phosphoric acid, sulfuric acid, boric acid, hydrofluoric acid, and hydrobromic acid, provided that the acid does not produce unwanted systemic side effects and is pharmaceutically acceptable when administered with the methods described herein. Exemplary examples of organic acids include, but are not limited to, lactic acid, acetic acid, formic acid, citric acid and oxalic acid.

In one embodiment of this aspect and all other aspects described herein, the inflammatory disorder is selected from the group consisting of: pulmonary fibrosis, inflammatory bowel disease, allergic diseases, arthritis and asthma (all of which involve potential contributions from the cys-LTs).

In another embodiment of this aspect and all other aspects described herein, the inflammatory disorder comprises asthma.

In another embodiment of this aspect and all other aspects described herein, the compound comprises a dextro-rotatory enantiomer of the formula:

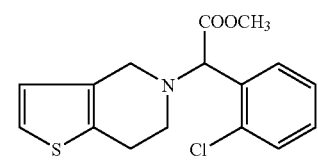

Another aspect described herein is a method for treating an inflammatory disorder in a subject, the method comprising administering to a subject having an inflammatory disorder a compound selected from the group consisting of dextro-rotatory isomer of methyl alpha-5(4,5,6,7-tetrahydro(3,2-c) thieno pyridyl)(2-chlorophenyl)-acetate substantially separated from the levorotatory isomer and its pharmaceutically acceptable salts, hydrochloride of the dextro-rotatory isomer of methyl alpha-5(4,5,6,7-tetrahydro(3,2-c)thieno pyridyl)(2-chlorophenyl)-acetate substantially separated from the levo-rotatory isomer, hydrogen sulfate of the dextro-rotatory isomer of methyl alpha-5(4,5,6,7-tetrahydro(3,2-c)thieno pyridyl)(2-chlorophenyl)-acetate substantially separated from the levo-rotatory isomer, hydrobromide of the dextro-rotatory isomer of methyl alpha-5(4,5,6,7-tetrahydro(3,2-c) thieno pyridyl)(2-chlorophenyl)-acetate substantially separated from the levo-rotatory isomer, and taurocholate of the dextro-rotatory isomer of methyl alpha-5(4,5,6,7-tetrahydro (3,2-c)thieno pyridyl)(2-chlorophenyl)-acetate substantially separated from the levo-rotatory isomer.

Definitions

As used herein, the term "therapeutically effective amount" refers to the amount of a thieno[3,2-c] pyridine derivative that is effective, at dosages and for periods of time necessary, to achieve the desired therapeutic result, e.g., a diminishment or prevention of symptoms associated with an inflammatory disorder such as asthma. A therapeutically effective amount of the inhibitors described herein, or functional derivatives thereof, may vary according to factors such as disease state, age, sex, and weight of the subject, and the ability of the therapeutic compound to elicit a desired response in the subject. The effective amount of a given therapeutic agent will also vary with factors such as the nature of the agent, the route of administration, the size and species of the mammal (e.g., human) to receive the therapeutic agent, and the purpose of the administration. A therapeutically effective amount is also one in which any toxic or detrimental effects of the therapeutic agent are outweighed by the therapeutically beneficial effects. The effective amount in each individual case may be determined empirically by a skilled artisan according to established methods in the art. In general, an inhibitor is determined to be "therapeutically effective" in the methods described herein if (a) a measurable symptom(s) of disease is reduced, e.g., a reduction in the frequency or severity of asthma attacks by at least 10% compared to the measurement prior to treatment onset, (b) the progression of the disease is halted (e.g., patients do not worsen or develop more severe asthma symptoms requiring hospitalization, or (c) symptoms are reduced or even ameliorated, for example, by measuring a decrease in inflammation. In the case of asthma, a "decrease in inflammation" means a decrease in sputum eosinophils, or exhaled nitric oxide levels of at least 20% in a subject treated as described herein compared to the subject prior to treatment. In other embodiments, a "decrease in inflammation" means a decrease in sputum eosinophils or exhaled nitric oxide levels of at least 30%, at least 40%, at least 50%, at least 60%, at least 70%, at least 80%, at least 90%, at least 95%, at least 99%, or even 100% (i.e., absence of sputum eosinophils) in a treated subject compared to the level of sputum eosinophils or exhaled nitric oxide measured in the subject prior to treatment as described herein.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

BRIEF DESCRIPTION OF THE FIGURES

FIG. 8. Dose-dependent effects of LTE4 and LTD4 on ERK activation in CHO cells. Cells were stably transfected with the human P2Y12 construct and stimulated for 15 minutes with the indicated ligand concentrations. The lanes displayed are from a single autoradiograph from one experiment. Results in a second experiment were similar.

DETAILED DESCRIPTION

Figure 1A:
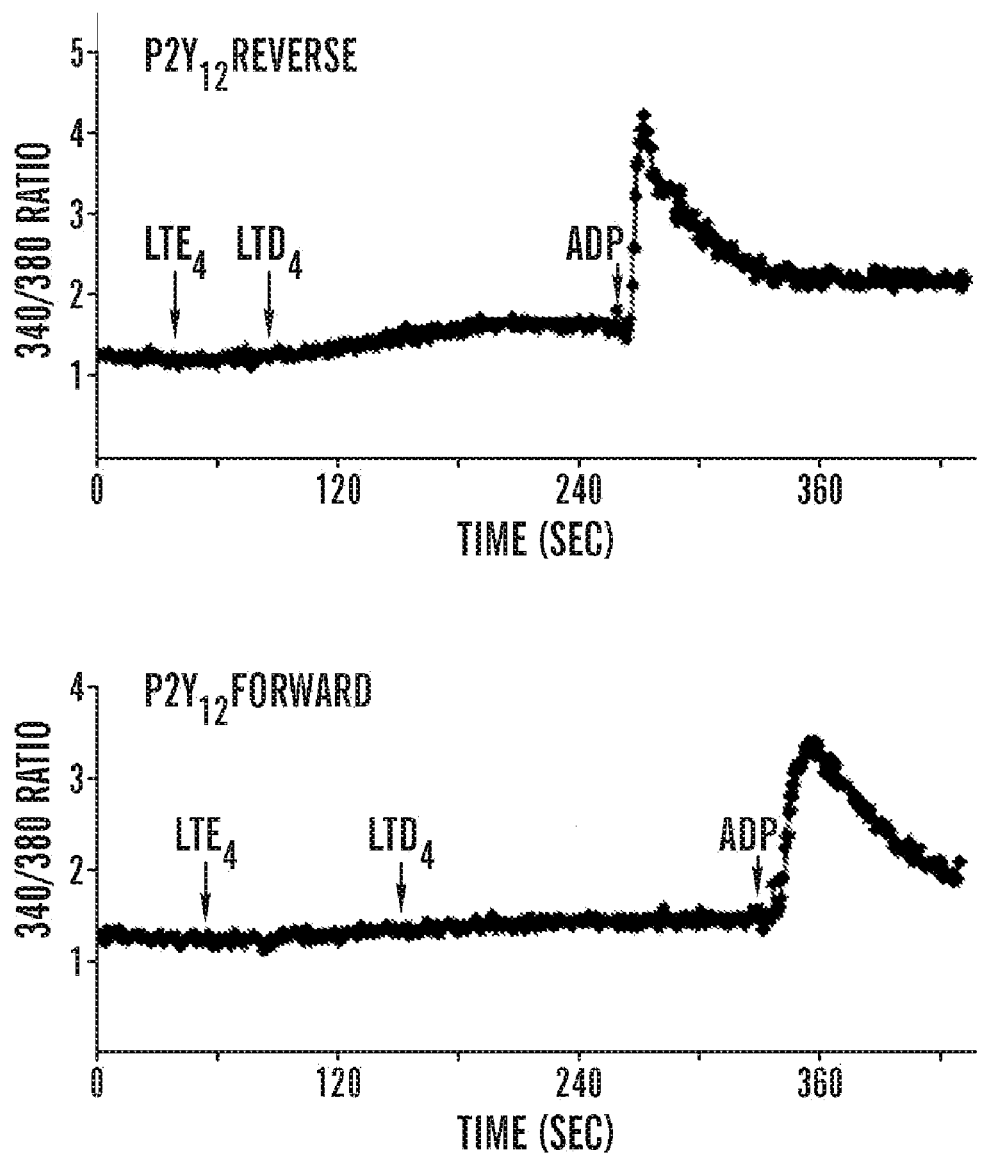
FIG. 1. Activation by recombinant human P2Y12 receptors in response to cys-LTs. The human P2Y12 receptor cDNA was cloned in forward and reverse orientation into the expression vector pEF1/His B and transfected into CHO cells using Fugene HD reagent. Stably-expressing clones were selected using G418 (1000 µg/ml), and expression of the construct was confirmed by cytofluorographic detection of the HIS tag. 1A. Calcium fluxes in CHO transfectants in response to LTE4, LTD4 (500 nM each) and ADP (100 µM). Results in second experiment were identical. 1B. SDS-PAGE immunoblots showing phosphorylation of ERK2 by CHO cells stably expressing human P2Y12 receptors in reverse (negative control) or forward orientations. Cells were stimulated with ADP (positive control ligand, 100 µM), LTD4 (500 nM) or LTE4 (500 nM) for 15 min. The blots were stripped and re-probed with an antibody (Ab) recognizing total ERK1 and ERK2. Dose-responses are displayed in FIG. 8. 1C. Effect of the selective P2Y12 receptor antagonist 2-MesAMP (MeS) on ligand-induced ERK phosphorylation. P2Y12 receptor expressing CHO cells were stimulated with the same doses of agonists used in 1A, in the absence or presence of 2-MesAMP (100 µM). 1D. Comparison of P2Y12 receptor-mediated responses to cys-LTs with those of recombinant human CysLT1R and CysLT2R expressed in CHO cells, and the effect of the CysLT1R antagonist MK571 (1 µM). Data in 1B-1D are from individual experiments that were repeated at least 3 times with similar results.

Described herein are methods and embodiments for treating inflammatory disorders by administering a compound that is a derivative of thieno[3,2-c] pyridine to a subject in need thereof.

Thieno[3,2-c] pyridine Derivatives

Thieno[3,2-c] pyridine derivatives having the following formula are useful for the methods described herein:

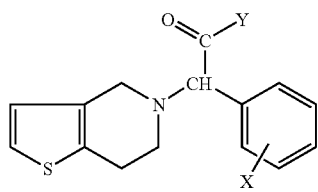

in which, Y represents the OH group or an OR group in which R is a straight or branched lower alkyl radical, or Y represents a group

in which $R_1$ and $R_2$ are each independently of each other hydrogen or a straight or branched lower alkyl group; or $R_1$ or $R_2$ form together and with the nitrogen atom to which they are attached a heterocycle which may include a second heteroatom such as oxygen or nitrogen, wherein the latter may be substituted by a lower alkyl or benzyl radical which may be substituted; and X represents hydrogen, a halogen or a lower alkyl radical.

These compounds having an asymmetrical carbon may exist in the form of two enantiomers. It is contemplated herein that each enantiomer and/or their mixture can be used with the methods described herein. The compounds also include addition salts with pharmaceutically acceptable mineral or organic acids if Y represents the group OR or

or with mineral bases if Y represents OH.

A "lower alkyl radical" is understood to mean a linear or branched $C_1$-$C_4$ saturated or unsaturated hydrocarbon chain. For example, methyl, ethyl, propyl, butyl, methyl-propyl, 2-methylpropyl and t-butyl.

Thieno[3,2-c] pyridine derivatives (e.g., clopidogrel bisulfate) and methods for making are described in the following US patents, which are incorporated herein by reference in their entirety: U.S. Pat. Nos. 4,529,596; 7,329,751; 7,153,969; 7,074,928; 7,060,831; 7,018,990; 6,800,759; 6,767,913; 6,737,411; 6,635,763; 5,189,170; 4,847,265; and 4,681,888, among others.

In one embodiment, the dextro-rotatory enantiomer of methyl alpha-5 (4,5,6,7-tetrahydro (3,2-c) thieno pyridyl)(2-chlorophenyl)-acetate) is used for the methods herein and has the following formula:

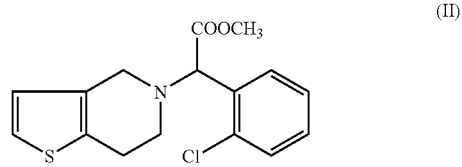

This compound is commercially available under the name PLAVIX® (clopidogrel bisulfate) from BRISTOL-MYERS SQUIBB™/SANOFI AVENTIS™. PLAVIX® is described in e.g., U.S. Pat. No. 4,847,265, which is herein incorporated by reference in its entirety.

Inflammatory Disorders

Inflammation occurs when tissues are injured by viruses, bacteria, trauma, chemicals, heat, cold, allergens, or any other harmful stimulus. Chemicals including bradykinin, histamine, serotonin and others are released, attracting tissue macrophages and white blood cells to localize in an area to engulf and destroy foreign substances. During this process, chemical mediators such as TNFα are released, giving rise to inflammation. Inflammatory disorders are those in which the inflammation is sustained or chronic.

Immunoinflammatory disorders (e.g., rheumatoid arthritis, psoriasis, ulcerative colitis, Crohn's disease, stroke-induced brain cell death, ankylosing spondylitis, fibromyalgia, and autoimmune diseases such as asthma, multiple sclerosis, type I diabetes, systemic lupus erythematosus, scleroderma, systemic sclerosis, and Sjogren's syndrome) are inflammatory disorders characterized by dysregulation of the immune system and inappropriate mobilization of body's defenses against its own healthy tissue.

In one embodiment, the inflammatory disorder comprises asthma. In asthma, chronic inflammatory processes in the airway play a central role in increasing the resistance to airflow within the lungs. Many cells and cellular elements are involved in the inflammatory process, particularly mast cells, eosinophils, T lymphocytes, neutrophils, epithelial cells, platelets, and even airway smooth muscle itself. The reactions of these cells result in an associated increase in the existing sensitivity and hyper-responsiveness of the airway smooth muscle cells that line the airways to the particular stimuli involved.

The chronic nature of asthma can also lead to remodeling of the airway wall (i.e., structural changes such as thickening or edema) which can further affect the function of the airway wall and influence airway hyper-responsiveness. Other physiologic changes associated with asthma include excess mucus production, and if the asthma is severe, mucus plugging, as well as ongoing epithelial denudation and repair. Epithelial denudation exposes the underlying tissue to substances that would not normally come in contact with them, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

Dosage and Administration

In one aspect, the present invention provides a method for treating inflammatory disorders, such as asthma in a subject. In one embodiment, the subject can be a mammal. In another embodiment, the mammal can be a human, although the invention is effective with respect to all mammals. The method comprises administering to the subject an effective amount of a pharmaceutical composition comprising thieno [3,2-c] pyridine derivative or a portion thereof, in a pharmaceutically acceptable carrier.

The dosage ranges for the agent depends upon the potency, and are amounts large enough to produce the desired effect e.g., a reduction in symptoms of asthma. The dosage should not be so large as to cause adverse side effects. Generally, the dosage will vary with the age, condition, and sex of the patient and can be determined by one of skill in the art. The dosage can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy.

A therapeutically effective amount is an amount of an agent that is sufficient to produce a statistically significant, measurable change in a symptom of disease (e.g., asthma) (see "Efficacy Measurement" below). Such effective amounts can be gauged in clinical trials as well as animal studies.

An agent can be administered intravenously by injection or by gradual infusion over time. Agents useful in the invention can be administered intravenously, intranasally, orally, by inhalation, intraperitoneally, intramuscularly, subcutaneously, intracavity, and can be delivered by peristaltic means, if desired, or by other means known by those skilled in the art. It is preferred that the compounds used herein are administered orally, intranasally, or by inhalation to a patient having an inflammatory disorder.

Therapeutic compositions containing at least one agent can be conventionally administered orally, intravenously, or by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

An agent may be adapted for catheter-based delivery systems including coated balloons, slow-release drug-eluting stents or other drug-eluting formats, microencapsulated PEG liposomes, or nanobeads for delivery using direct mechanical intervention with or without adjunctive techniques such as ultrasound.

In some embodiments, an inhibitor may be combined with a therapeutically effective amount of another therapeutic agent for treatment of inflammatory disorders. For example, in the treatment of asthma a thieno[3,2-c] pyridine derivative compound may be combined with a therapeutically effective amount of e.g., a glucocorticoid (e.g., ciclesonide, beclomethasone, budesonide, flunisolide, fluticasone, mometasone, and triamcinolone), a leukotriene modifier (e.g., montelukast, zafirlukast, pranlukast, and zileuton), a mast cell stabilizer (e.g., cromoglicate (cromolyn), and nedocromil), antimuscarinics/anticholinergics (e.g., ipratropium, oxitropium, and tiotropium), a methylxanthine (theophylline and aminophylline), an antihistamine, an IgE blocker (e.g., Omalizumab), methotrexate, salbutamol, terbutaline, a systemic steroid (e.g., prednisone, prednisolone, methylprednisolone, dexamethasone, or hydrocortisone), a non-specific beta agonist (e.g., epinephrine, isoetharine, isoproterenol, metaproterenol), and/or an anti-cholinergic (e.g., glycopyrrolate, atropine, ipratropium) agent.

Pharmaceutical Compositions

The present invention involves therapeutic compositions useful for practicing the therapeutic methods described herein. Therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

Efficacy Measurement

The efficacy of a given treatment for an inflammatory disorder can be determined by the skilled clinician. However, a treatment is considered "effective treatment," as the term is used herein, if any one or all of the signs or symptoms of e.g., asthma are altered in a beneficial manner, other clinically accepted symptoms are improved, or even ameliorated, e.g., by at least 10% following treatment with a thieno[3,2-c] pyridine derivative. Efficacy can also be measured by a failure of an individual to worsen as assessed by hospitalization or need for medical interventions (i.e., progression of the disease is halted). Methods of measuring these indicators are known to those of skill in the art and/or are described herein. Treatment includes any treatment of a disease in an individual or an animal (some non-limiting examples include a human, or a mammal) and includes: (1) inhibiting the disease, e.g., arresting the frequency of further attacks; or (2) relieving the disease, e.g., causing regression of symptoms, improving lung function, halting the progressive decline in lung function and/or reducing asthma related mortalities; (3) preventing acute disease onset such as e.g., an initiating asthma attack.

An effective amount for the treatment of a disease means that amount which, when administered to a mammal in need thereof, is sufficient to result in effective treatment as that term is defined herein, for that disease. Efficacy of an agent can be determined by assessing physical indicators of, for example asthma, such as e.g., airway reactivity, inflammation, broncho-constriction, lung volume capacity, exacerbation frequency, symptom scores, etc.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention may be as defined in any one of the following numbered paragraphs.

1. A method of treating an inflammatory disorder in a subject, the method comprising administering to a subject having an inflammatory disorder a therapeutically effective amount of a compound having the formula:

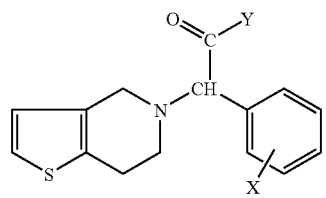

in which Y represent hydroxyl, an OR group wherein R is a straight or branched lower alkyl radical, or

in which $R_1$ and $R_2$ are each independent of each other and represent hydrogen or a straight or branched lower alkyl group; or $R_1$ and $R_2$ form together with the nitrogen atom to which they are attached a heterocycle, selected from the group consisting of pyrrolidino, piperidino, morpholino, piperazino, N-lower alkyl piperazino; and X represents hydrogen, a halogen or a lower alkyl radical; and their addition salts with pharmaceutically acceptable mineral or organic acids if Y represents the group OR or

or with mineral bases if Y represents OH, including both enantiomeric forms or their mixture.

2. The method of paragraph 1, wherein the inflammatory disorder is selected from the group consisting of: pulmonary fibrosis, inflammatory bowel disease, allergic diseases, arthritis and asthma.

3. The method of paragraph 1, wherein the inflammatory disorder comprises asthma.

4. The method of paragraph 1, wherein the compound comprises a dextro-rotatory enantiomer of the formula:

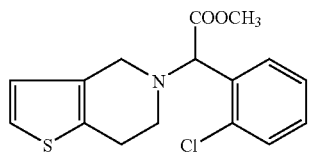

5. A method for treating an inflammatory disorder in a subject, the method comprising administering to a subject having an inflammatory disorder a compound selected from the group consisting of dextro-rotatory isomer of methyl alpha-5(4,5,6,7-tetrahydro(3,2-c)thieno pyridyl)(2-chlorophenyl)-acetate substantially separated from the levorotatory isomer and its pharmaceutically acceptable salts, hydrochloride of the dextro-rotatory isomer of methyl alpha-5(4,5,6,7-tetrahydro(3,2-c)thieno pyridyl)(2-chlorophenyl)-acetate substantially separated from the levo-rotatory isomer, hydrogen sulfate of the dextro-rotatory isomer of methyl alpha-5(4,5,6,7-tetrahydro(3,2-c)thieno pyridyl)(2-chlorophenyl)-acetate substantially separated from the levo-rotatory isomer, hydrobromide of the dextro-rotatory isomer of methyl alpha-5(4,5,6,7-tetrahydro(3,2-c)thieno pyridyl)(2-chlorophenyl)-acetate substantially separated from the levo-rotatory isomer, and taurocholate of the dextro-rotatory isomer of methyl alpha-5(4,5,6,7-tetrahydro(3,2-c)thieno pyridyl)(2-chlorophenyl)-acetate substantially separated from the levo-rotatory isomer.

EXAMPLES

The Examples described herein demonstrate that the $P2Y_{12}$ receptor, an adenosine diphosphate (ADP)-reactive GPCR that is the target of the thienopyridine anti-thrombotic drugs (Foster, C. J., et al. *J. Clin. Invest.* 107:1591-1598), is a bona fide $CysLT_3R$ that accounts for the unique functions of $LTE_4$ in vitro and in vivo. These results indicate that $P2Y_{12}$ receptors are a novel target for the treatment of asthma.

Example 1

Recombinant Human $P2Y_{12}$ Receptors Convey Responses to $LTE_4$

Figure 1D:
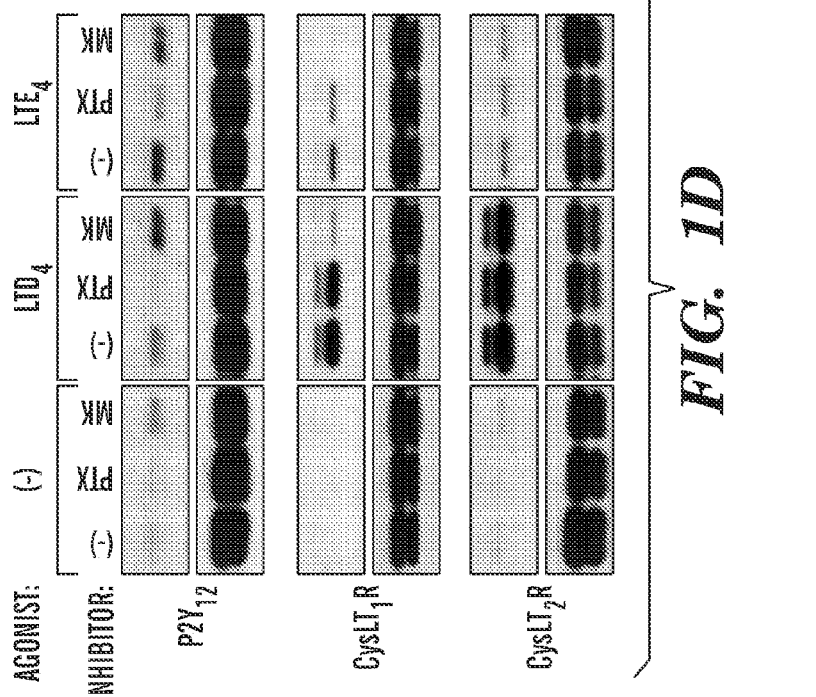
Figure 1B:
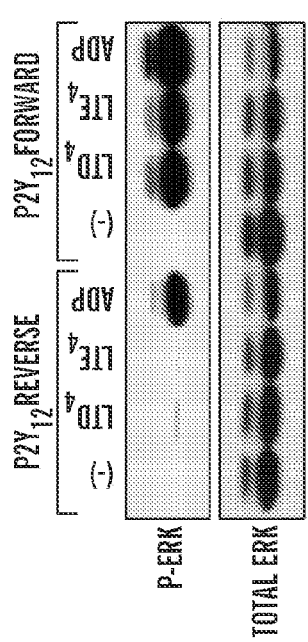
Figure 1C:
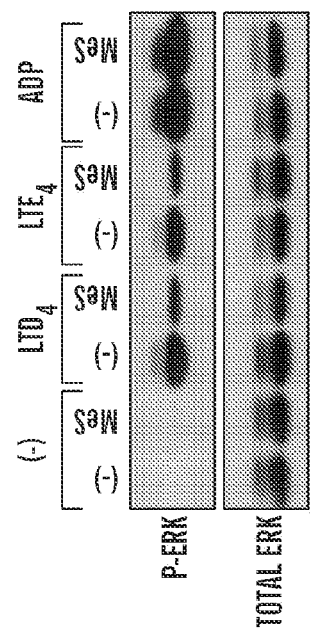

To determine if $P2Y_{12}$ receptors directly recognized $LTE_4$, Chinese Hamster Ovary (CHO) cells stably expressing the human $P2Y_{12}$ receptor protein were generated. This cell line does not express native CysLTRs (Maekawa, A., et al. 2001. *Proc. Natl. Acad. Sci. U.S.A.* 98:2256-2261). A $P2Y_{12}$ receptor cDNA was amplified by reverse transcriptase polymerase chain reaction (RT-PCR) from RNA extracted from primary hMCs and cloned into a mammalian expression vector. Expression was confirmed by detection of a histidine (HIS) tag by flow cytometry. Another cohort of CHO cells were stably transfected with a $P2Y_{12}$ receptor construct in reverse orientation as a negative control. The membranes of the transfectants bound $LTE_4$ with an affinity constant of 10 nM, and also bound $LTC_4$ and $LTD_4$. As anticipated, the membranes of CHO cells stably transfected with human $CysLT_1R$ and $CysLT_2R$ only weakly bound $LTE_4$. To determine whether expression of the cloned human $P2Y_{12}$ receptor conveyed signaling events in CHO cells, the transfectants were stimulated with exogenous $LTC_4$, $LTD_4$, or $LTE_4$. Fura-2-AM-loaded CHO cells expressing $CysLT_1R$, $CysLT_2R$, or $P2Y_{12}$ receptors failed to flux calcium in response to $LTE_4$, but did exhibit a response to ADP, reflecting endogenous P2Y receptors (FIG. 1A). In contrast, $P2Y_{12}$-expressing CHO cells responded to both $LTD_4$ and $LTE_4$ with robust, dose-dependent ERK activation (FIG. 1B). The cys-LT-induced ERK activation blocked by pre-treatment of the cells with pertussis toxin (PTX), was attenuated by treatment with the $P2Y_{12}$ receptor-selective antagonist 2-methylthioadenosine monophosphate (2-MesAMP) (FIG. 1C), and was resistant to MK571, an inhibitor that blocks $CysLT_1R$ and some P2Y receptors (Mamedova, L., et al. 2005. *Biochem. Pharmacol.* 71:115-125). While ERK activation in the $P2Y_{12}$ receptor transfectants was at least as robust in response to $LTE_4$ as to $LTD_4$ (FIG. 1D), $CysLT_1R$ and $CysLT_2R$ transfectants reacted to $LTD_4$ in marked preference to $LTE_4$, even at high (500 nM) ligand concentrations. These responses were resistant to PTX and 2-MesAMP, and susceptible to MK571 in the case of the $CysLT_1R$ transfectants.

Example 2

$P2Y_{12}$ Receptors Account for the Activation of LAD2 Cells by $LTE_4$

Figure 2A:
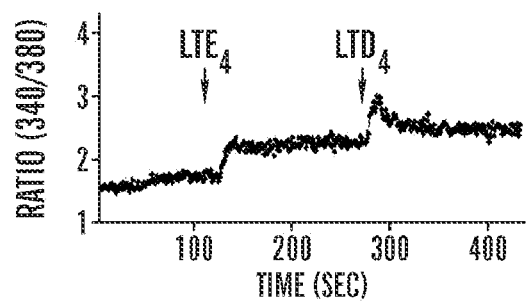
FIG. 2. Requirement for $P2Y_{12}$ receptors in $LTE_4$-mediated LAD2 cell activation. 2A. Calcium flux of LAD2 cells stimulated with the indicated agonists (500 nM) in the presence or absence of the P2Y12 receptor-selective antagonist 2-MeSAMP (100 µM). MK571 completely blocked both $LTD_4$- and $LTE_4$-mediated calcium fluxes (data not shown). 2B. Effect of 2-MeSAMP (100 µM), MK571 (1 µM) or both antagonists on MIP-1β generation by LAD2 cells in response to the indicated doses of $LTD_4$ and $LTE_4$. Cells sensitized overnight with IgE and challenged with anti-IgE were used as the positive control. 2C. Effect of shRNA-mediated knockdowns of $CysLT_1R$ or $P2Y_{12}$ receptors on MIP-1β generation (top) and $PGD_2$ generation (bottom) by LAD2 cells stimulated with $LTD_4$ or $LTE_4$ (100 nM each). Results in 2B and 2C are mean±SEM from three independent experiments each. 2D. Effect of shRNA-mediated knockdown of $P2Y_{12}$ receptor mRNA expression by LAD2 cells.
Figure 2A:
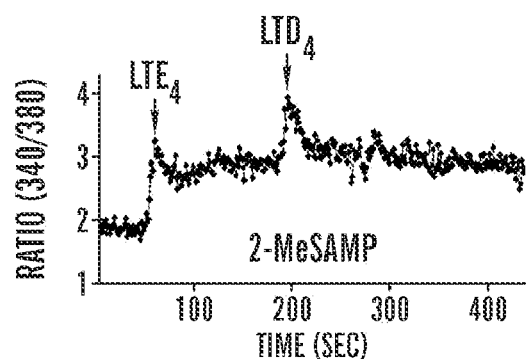
Figure 2A:
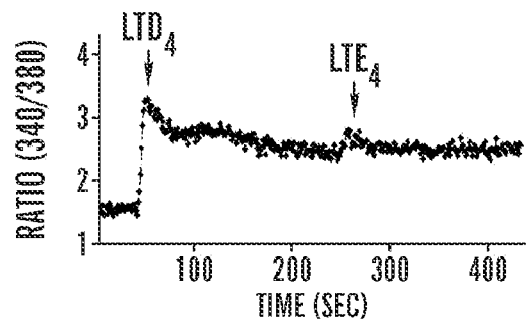
Figure 2A:
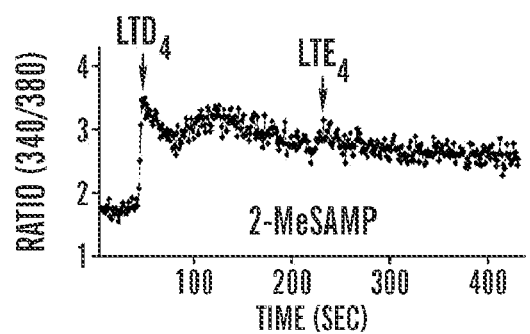
Figure 2B:
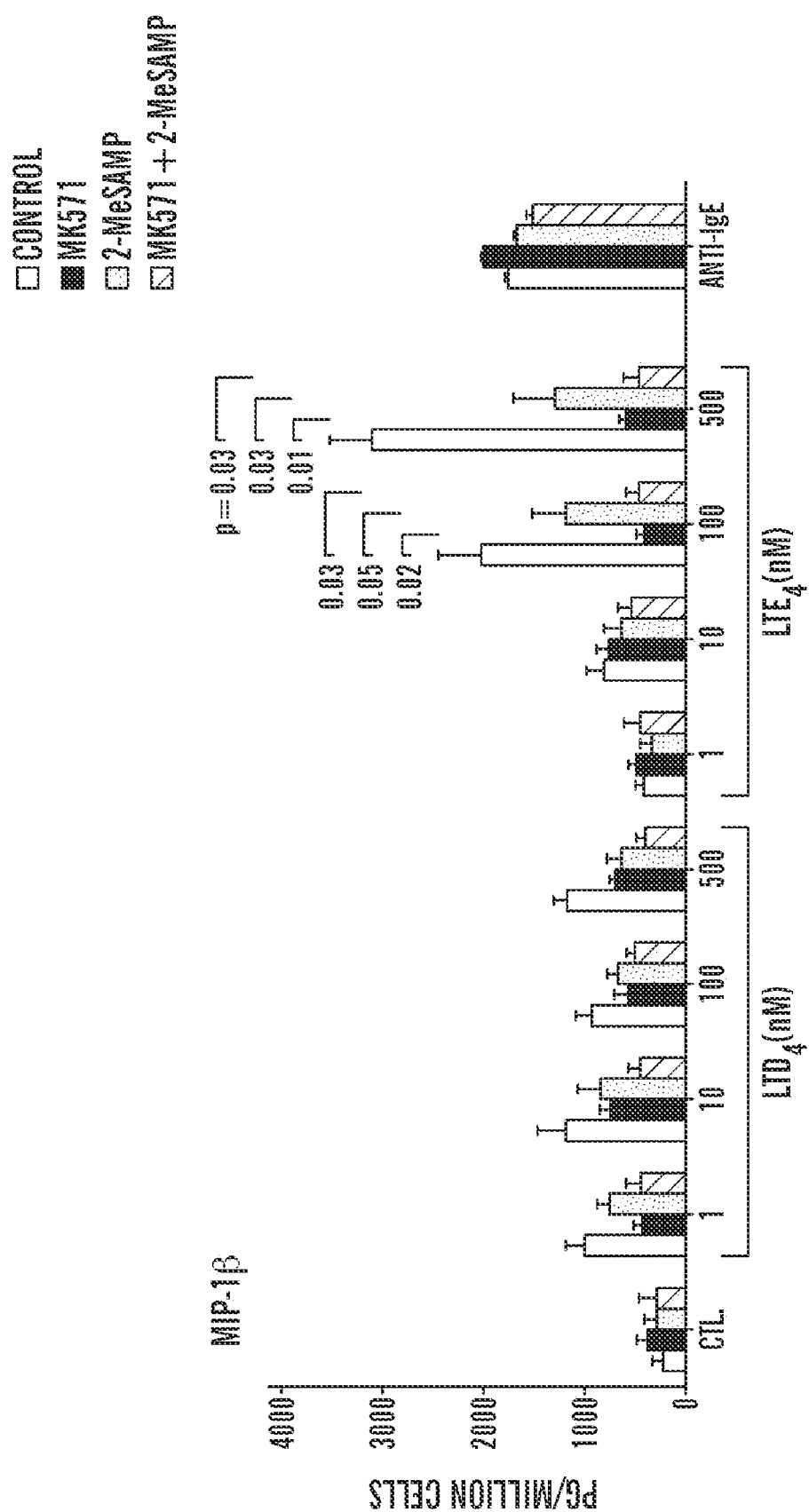
Figure 9A:
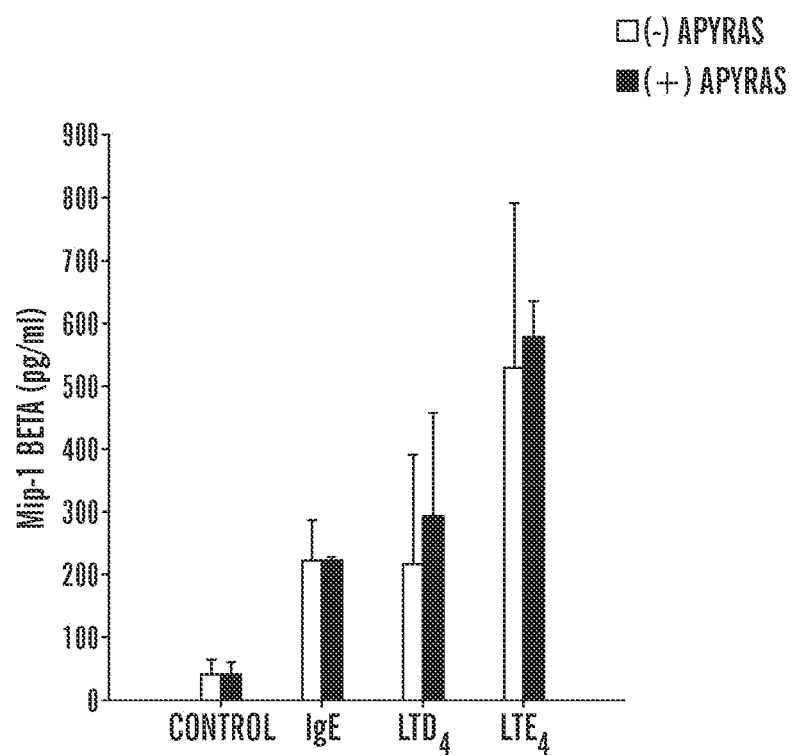
FIG. 9. Effect of apyrase treatment on LT-mediated activation of LAD2 cells. 9A. LAD2 cells were passively sensitized with human myeloma IgE and stimulated for 6 h with anti-IgE, or with LTD4 or LTE4 (500 nM) in the absence or presence of apyrase (10 µM). Concentrations of MIP-1β were measured by ELISA. 9B. LAD2 cells were stimulated for 15 minutes with LTD4, LTE4 (500 nM) or buffer (control) in the presence or absence of apyrase. Lysates were resolved by SDS-PAGE and probed with the indicated antibodies against phospho- and total ERK. Results in 9A are the mean±½ range from two experiments, while 9B is representative of two experiments.
Figure 9B:
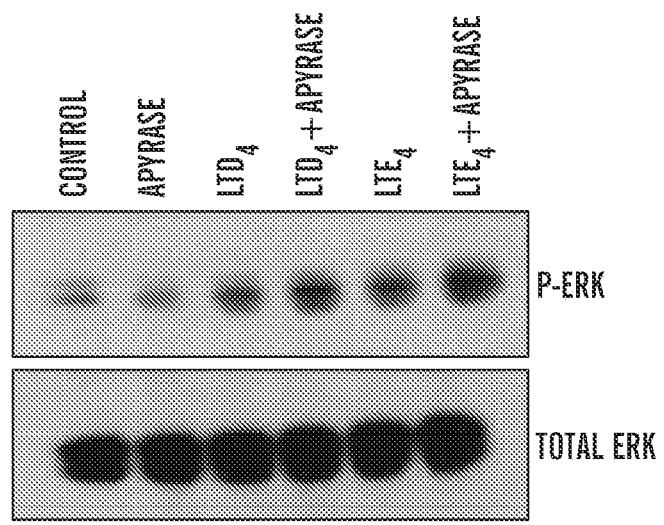

To determine whether $P2Y_{12}$ receptors account for the activation of MCs by exogenous $LTE_4$, Fura-2 AM-loaded LAD2 cells were stimulated with $LTD_4$ or $LTE_4$ in the presence or absence of 2-MesAMP or MK571. As reported previously (Paruchuri, S., et al. 2008. *J. Biol. Chem.* 283:16477-16487), MK571 blocked calcium responses of LAD2 cells to both ligands (data not shown). In contrast, 2-MesAMP treatment failed to attenuate $LTD_4$- or $LTE_4$-mediated calcium flux in LAD2 cells (FIG. 2A). The effect of MK571 and 2-MesAMP on MIP-1β generation by LAD2 cells in response to stimulation for 6 h with $LTD_4$ and $LTE_4$ was determined, using IgE plus anti-IgE as positive control. $LTE_4$ at doses of 100 and 500 nM induced the generation of large amounts of MIP-1β, exceeding the responses to $LTD_4$ and to IgE plus anti-IgE (FIG. 2B). Pre-treatment of the LAD2 cells with 2-MesAMP blocked the $LTE_4$-mediated increment in MIP-1β production by >50% (FIG. 2B). 2-MesAMP also reduced the response to the higher concentrations of $LTD_4$. MK571 suppressed the response to both ligands, and was additive with 2-MesAMP for the suppression of the response to $LTD_4$. Neither antagonist altered the production of MIP-1β in response to $LTD_4$ or to IgE plus anti-IgE. To exclude potential off-target effects of the inhibitors, samples of LAD2 cells were transfected with lentiviruses encoding a $P2Y_{12}$ sequence-specific shRNA, a $CysLT_1R$-specific shRNA, or an empty vector control before stimulation. Knockdown of $P2Y_{12}$ receptors was highly efficacious, decreasing the receptor mRNA expression by ~90% (FIG. 2D), and did not alter expression of $CysLT_1R$ protein (data not shown). $P2Y_{12}$ receptor knockdown nearly abrogated MIP-1β production in response to $LTE_4$, and had minimal effect on the response to $LTD_4$. The response to $LTD_4$ was completely blocked by knockdown of $CysLT_1R$, which tended to decrease MIP-1β production in response to $LTE_4$, but the latter effect did not reach statistical significance. $LTE_4$- and $LTD_4$-dependent production of $PGD_2$ were abrogated by the knockdowns of $P2Y_{12}$ and $CysLT_1R$, respectively (FIG. 2C, bottom). Neither GPCR knockdown altered MIP-1β generation or $PGD_2$ production in response to IgE-anti-IgE (FIG. 2C). LTE4-mediated MIP-1β generation (FIG. 9A) and ERK activation (FIG. 9B) were not altered by treatment of LAD2 cells with apyrase to degrade extracellular ADP.

Figure 10A:
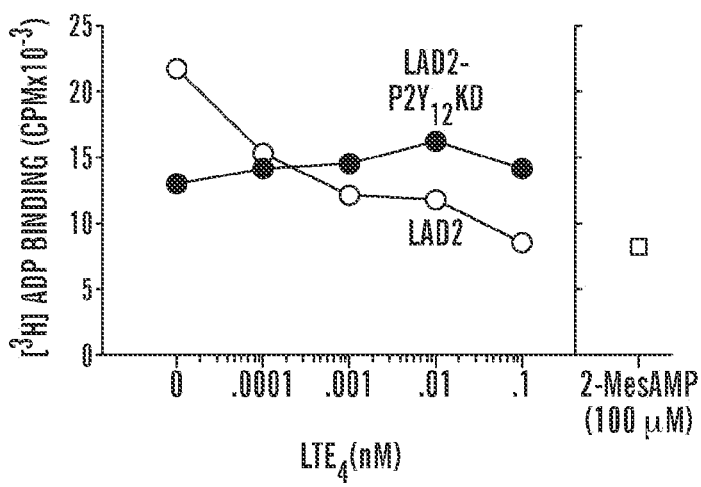
FIG. 10. Competitive ligand binding assays. 10A. Dose-dependent competition of unlabeled LTE4 at the indicated doses for binding of radiolabeled ADP (2000 nM) to the membranes of LAD2 cells with and without shRNA-mediated knockdown of P2Y12 receptors in the indicated samples. Specific binding (typically 50-75% of the total) was calculated by subtracting the amount of radiolabel that was insensitive to the selective P2Y12 receptor antagonist 2-MesAMP. Nonspecific binding was essentially identical in the membranes with and without P2Y12 receptor knockdown. The dose response for the LAD2 membranes are from a single experiment repeated four times with similar results. The binding on the LAD2 cells with P2Y12 knocked down was repeated twice. 10B. Specific binding of radiolabeled ADP (2000 nM) to membranes of LAD2 cells. Unlabeled LTD4 and LTE4 (10 µM) were used as competitors. Results are mean±SD from three separate experiments. 10C. Conversion of radiolabeled LTD4 to LTE4 as confirmed by HPLC (left). PGB2 is used as the internal standard for the HPLC, with LTD4 and LTE4 eluting at ~23.5 and 24.3 minutes, respectively. Binding of [³H]LTE4 (converted from LTD4) to membranes of LAD2 cells with and without knockdown of P2Y12 receptors. Results in a second experiment were similar 10D. Competitive binding of radiolabeled 2-MesADP to COS-7 cells transfected with the human P2Y12 construct.
Figure 10B:
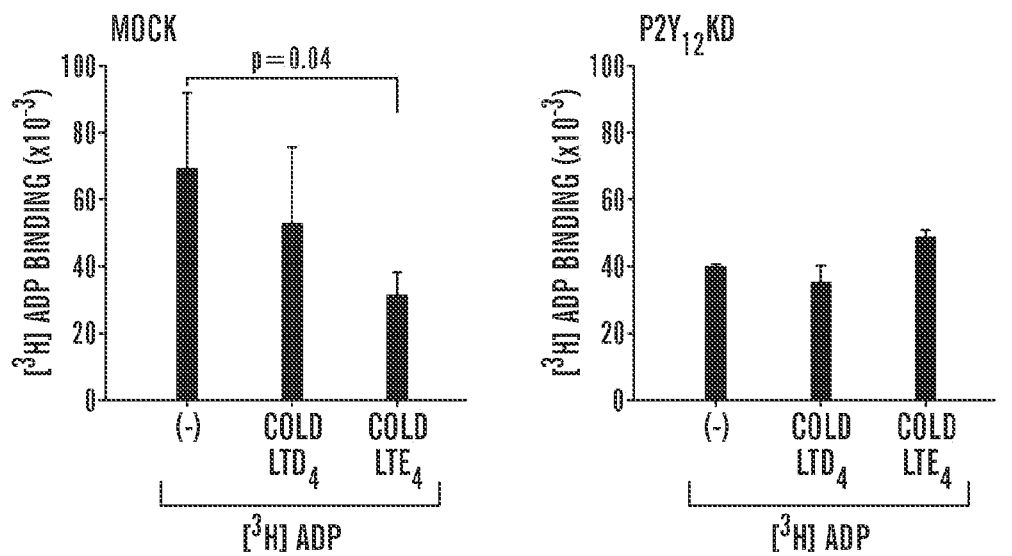
Figure 10C:
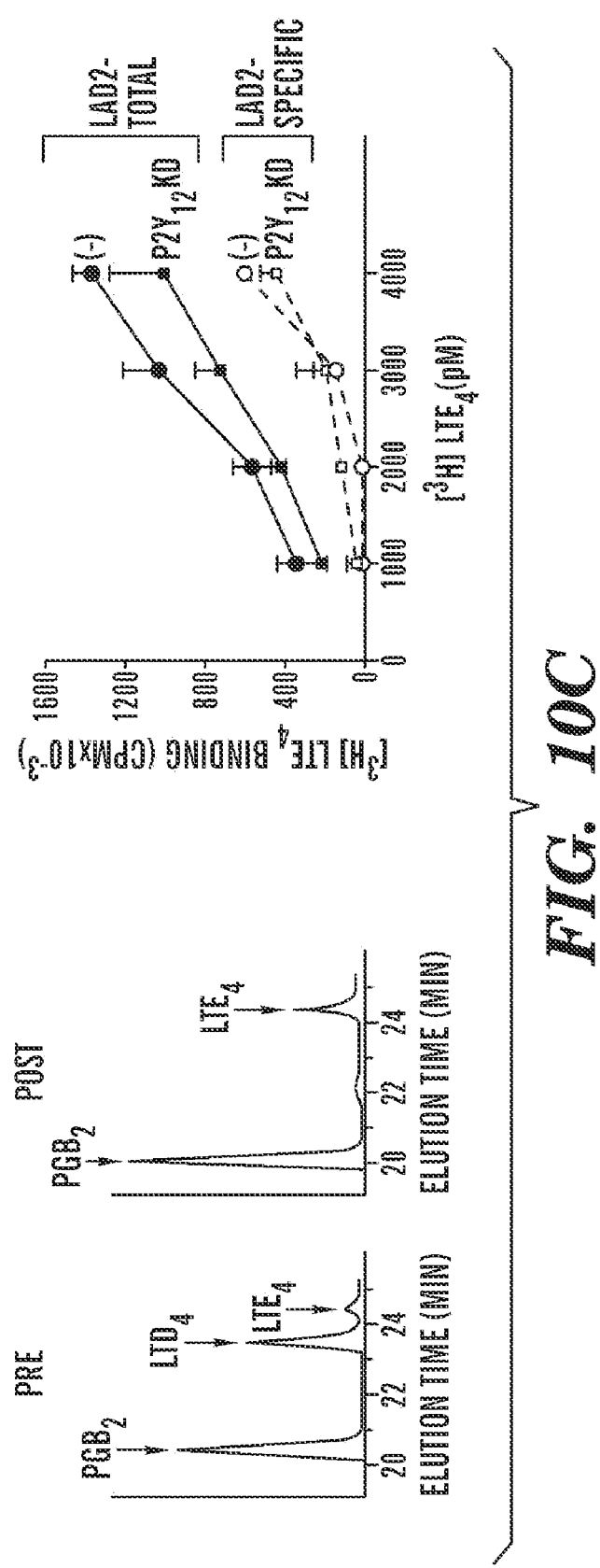
Figure 10D:
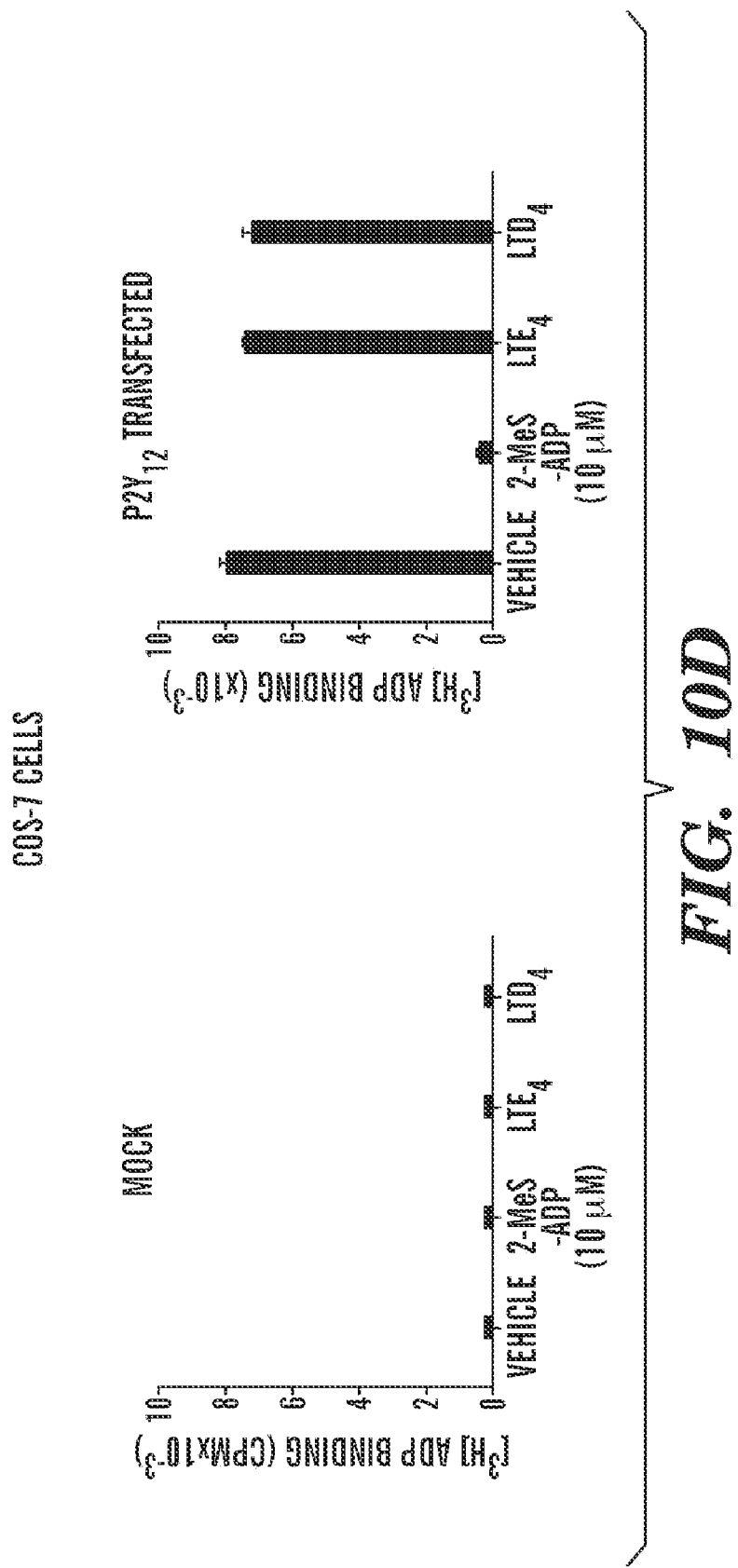

To determine whether $P2Y_{12}$ receptors directly mediated $LTE_4$ binding, membranes were prepared from LAD2 cells with and without $P2Y_{12}$ knockdown. Competitive radioligand binding assays were performed using [$H^3$]ADP (the known natural ligand of $P2Y_{12}$ receptors) and unlabeled LTs as competitors. Unlabeled $LTE_4$ competed with labeled ADP, blocking 39±9% and 50±9% of specific ADP binding at doses of 0.1 and 1 nM, respectively, and reaching a plateau (60±7%) at 1 μM (mean±SEM for four separate experiments, as shown for one experiment, FIG. 10A). $LTE_4$ was more efficacious than $LTD_4$ (FIG. 10B). Knockdown $P2Y_{12}$ receptors reduced binding of [$H^3$]ADP by 40-60%, and completely eliminated competition $LTE_4$ (FIGS. 10A and 10B, right panel). LAD2 cell membranes weakly bound [$H^3$]$LTE_4$ (converted from commercially prepared [$H^3$]$LTD_4$, FIG. 10C), but specific binding of [$H^3$]$LTE_4$ was not altered by the knockdown of $P2Y_{12}$ receptor (FIG. 10C). To determine whether $LTE_4$ could block the ADP binding of $P2Y_{12}$ receptors expressed in isolation, the human forward and reverse $P2Y_{12}$ constructs were transiently expressed in COS-7 cells. The membranes from the transfectants expressing the forward construct bound [$P^{33}$]2-MesADP, a selective $P2Y_{12}$ receptor agonist. In contrast to ADP binding to LAD2 membranes, this binding was not competed unlabeled $LTE_4$ or $LTD_4$ (FIG. 10D). Additionally, these membranes failed to bind [$H^3$]$LTE_4$ (not shown).

Example 3

Figure 3A:
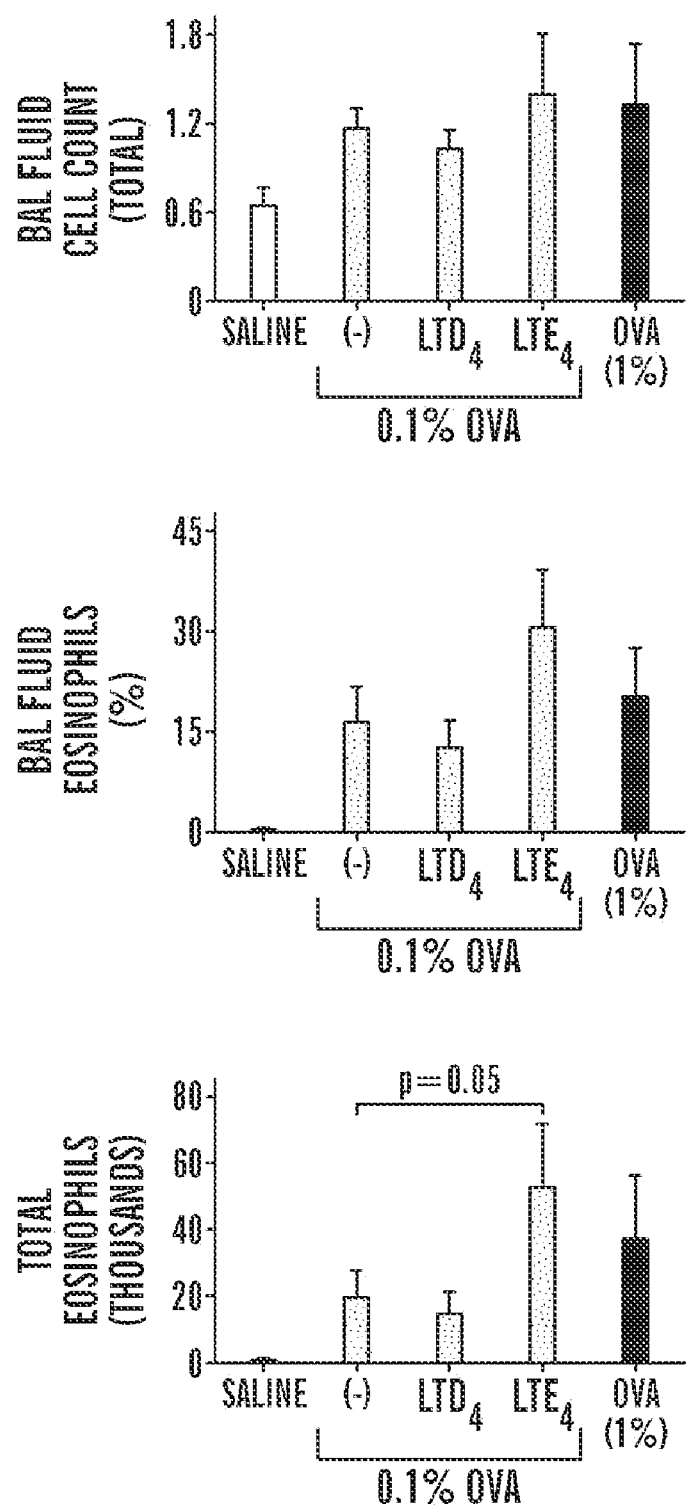
FIG. 3. $LTE_4$-mediated amplification of allergen-induced pulmonary inflammation. 3A. BAL fluid total cell counts (top) with percentages (middle) and total numbers (bottom) of eosinophils. Mice were sensitized twice with alum-precipitated ovalbumin (OVA). $LTD_4$ or $LTE_4$ (1 µg) were administered intranasally 12 hours before each of three challenges with 0.1% OVA. A separate sensitized group of mice were treated with 1% OVA as a positive control. 3B. Quantitative analysis if pulmonary inflammation, measured as the number of bronchovascular bundles with cellular infiltrates per 15 such bundles per mouse. 3C. Representative fields of H & E-stained lungs from mice from the indicated experimental groups. 3D. Morphometric analysis of goblet cell metaplasia, measured as the numbers of PAS-positive cells per mm of bronchial basal lamina. 3E. Representative PAS stains showing goblet cells (arrows). Results in 3A, 3B, and 3D are mean±SEM from 8-9 mice per group.
Figure 3B:
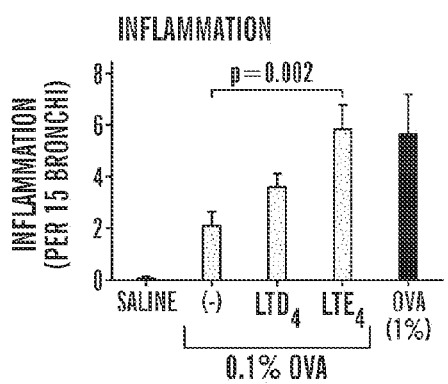
Figure 3C:
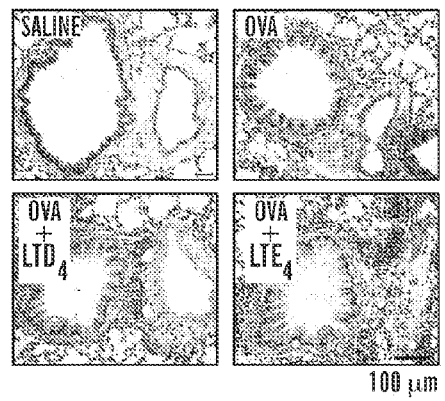
Figure 3D:
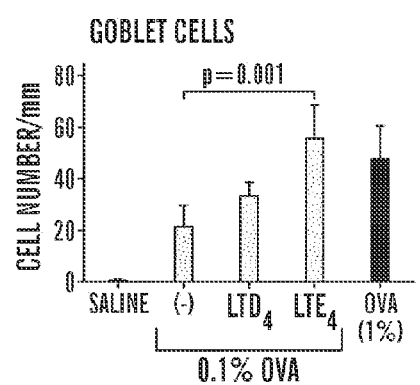
Figure 3E:
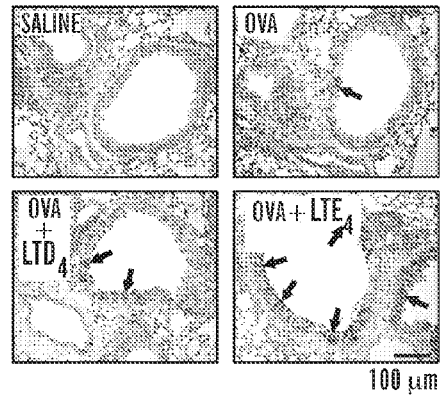

$LTE_4$ Strongly Potentiates Allergen-Induced Bronchial Inflammation Independently of Classical cys-LT Receptors To determine whether $LTE_4$ could induce or potentiate histologic signatures of pulmonary inflammation in mice, the effect of intranasal $LTE_4$ (2 nmol) administered on three successive days on the lung histology of naïve BALB/c mice was determined. The effect was compared to that of $LTD_4$. The lungs of naïve BALB/c mice showed no evidence of cellular influx or goblet cell metaplasia after three doses of either cys-LT (not shown). Thus, it was sought to determine whether either cys-LT amplified pulmonary inflammation induced by the inhalation of low-dose allergen in sensitized mice. Two weeks after sensitization with chicken egg ovalbumin (OVA) by intraperitoneal injection, BALB/c mice received inhalation challenges on three consecutive days with low-dose OVA (0.1%) for 30 minutes. Twelve hours before each challenge, the mice received intranasal $LTD_4$, $LTE_4$, or a buffer control. A cohort of mice treated with 1% OVA were maintained as a positive control. The mice were then euthanized, their BAL fluid collected, and their lungs examined histologically for evidence of inflammation and goblet cell metaplasia, a dominant pathologic signature of Th2-polarized mucosal inflammation. Compared to saline-treated, sensitized mice, mice challenged with low-dose OVA demonstrated low-grade BAL fluid eosinophilia (FIG. 3A). These mice treated with low-dose OVA showed very mild pulmonary inflammation, as indicated by the accumulation of lymphocytes, plasma cells, and eosinophils around the bronchovascular bundles (FIG. 3B, as shown in 3C). The administration of $LTD_4$ did not increase BAL fluid eosinophilia (FIG. 3A), and tended to slightly potentiate both bronchovascular inflammation (FIG. 3B, FIG. 3C) and goblet cell metaplasia (FIGS. 3D, 3E). In contrast, $LTE_4$ significantly enhanced BAL fluid eosinophilia (FIG. 3A), inflammation (FIGS. 3B, 3C) and goblet cell metaplasia (FIGS. 3D, 3E). The extent of the cellularity and goblet cell responses of the $LTE_4$-treated animals approached the levels of these parameters in the mice treated with 1% OVA.

To determine whether $LTE_4$-induced amplification of pulmonary inflammation required the presence of $CysLT_1R$ and/or $CysLT_2R$, the experiments were repeated in OVA sensitized and challenged BALB/c mice lacking both $CysLT_1R$ and $CysLT_2R$ (double $CysLTR^{-/-}$ mice). These mice were generated through intercrosses of $CysLT_1R^{-/-}$ and $CysLT_2R^{-/-}$ mice that had both been backcrossed to the BALB/c background for ten generations. Due to limited numbers of available mice, all animals were sensitized and challenged with low-dose OVA, and half were treated with exogenous $LTE_4$. Strikingly, the potentiation of OVA-induced BAL fluid eosinophilia (FIG. 4G), goblet cell metaplasia (FIG. 4E) and inflammation (FIG. 4F) by $LTE_4$ were completely intact in the double-null mice, indicating that $LTE_4$ was working independently of the known GPCRs for cys-LTs.

Example 4

Figure 5A:
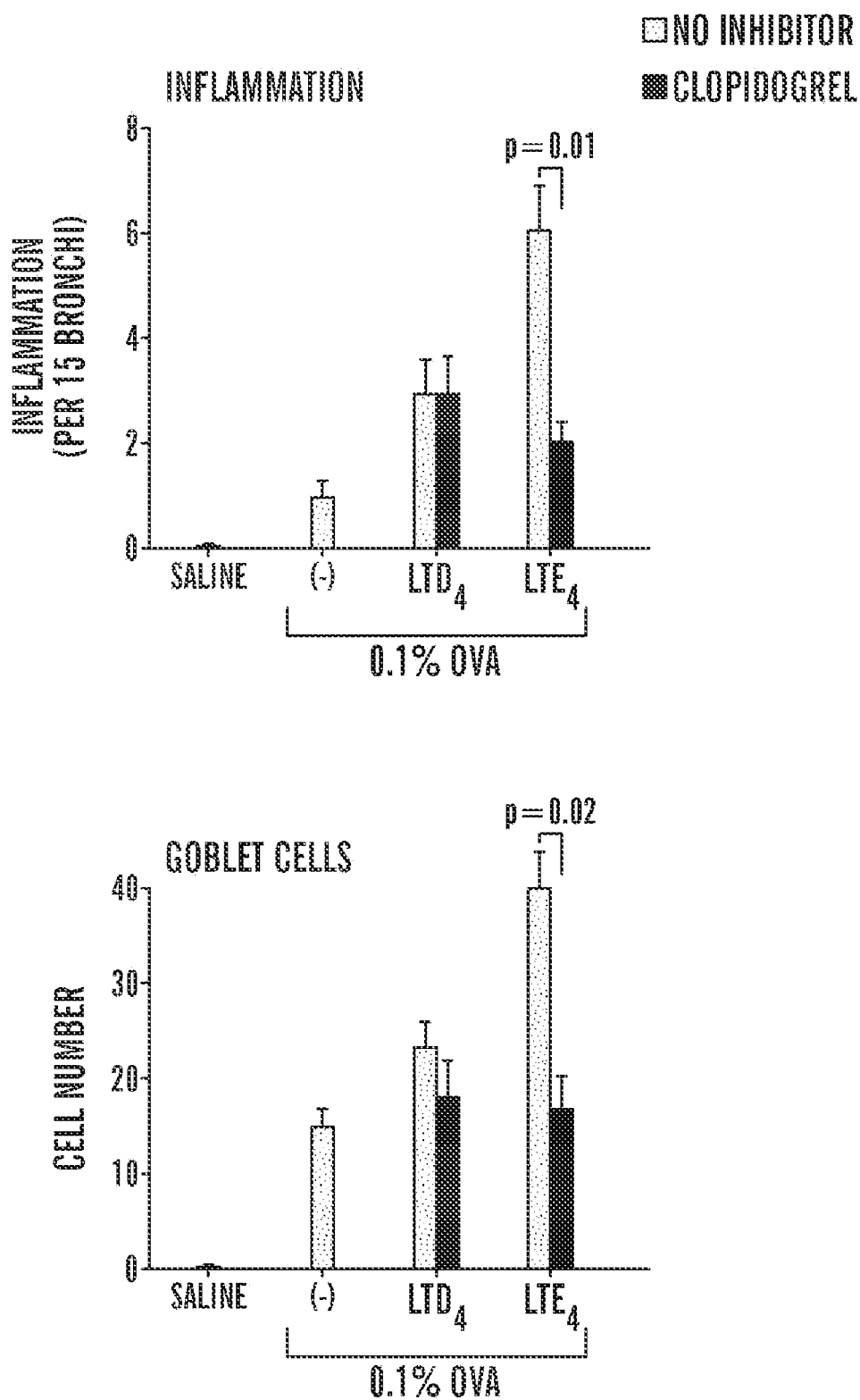
FIG. 5. Effect of clopidogrel on LTE$_4$-mediated amplification of pulmonary inflammation. 5A. Bronchovascular inflammation (top) and goblet cell metaplasia in sensitized mice challenged with low dose OVA with or without the prior administration of LTD$_4$ or LTE$_4$. The indicated mice were treated with clopidogrel for 72 h before the first dose of leukotriene. Results are mean±SEM from a minimum of 9 mice in each group. 5B. PAS stains (left column) from representative mice in the indicated groups showing the effect of clopidigrel on goblet cell metaplasia. Higher magnification images of H & E stains (right) from the same animals showing cellular characteristics of the bronchovascular infiltrates. 5C. Effect of clopidogrel administration on the steady-state expression of IL-13 and MUC5AC mRNA as determined by real-time PCR of whole lung RNA extracted 24 h after the last OVA challenge of the indicated groups. Data are mean±SEM from 4-5 mice/group.
Figure 5B:
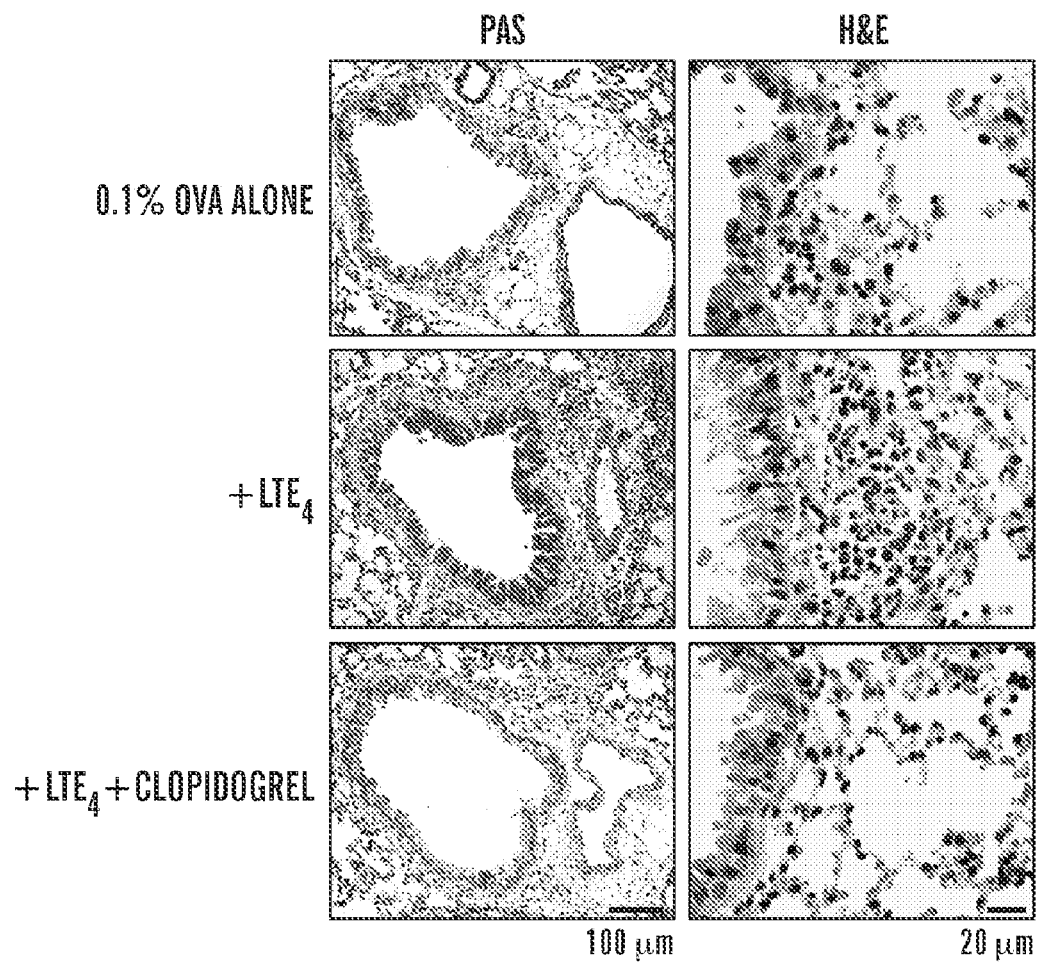
Figure 5C:
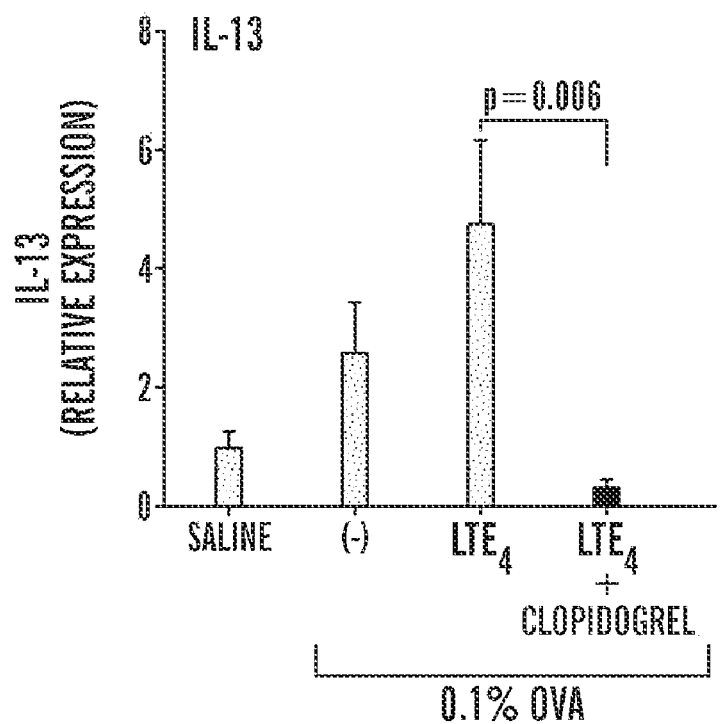
Figure 5C:
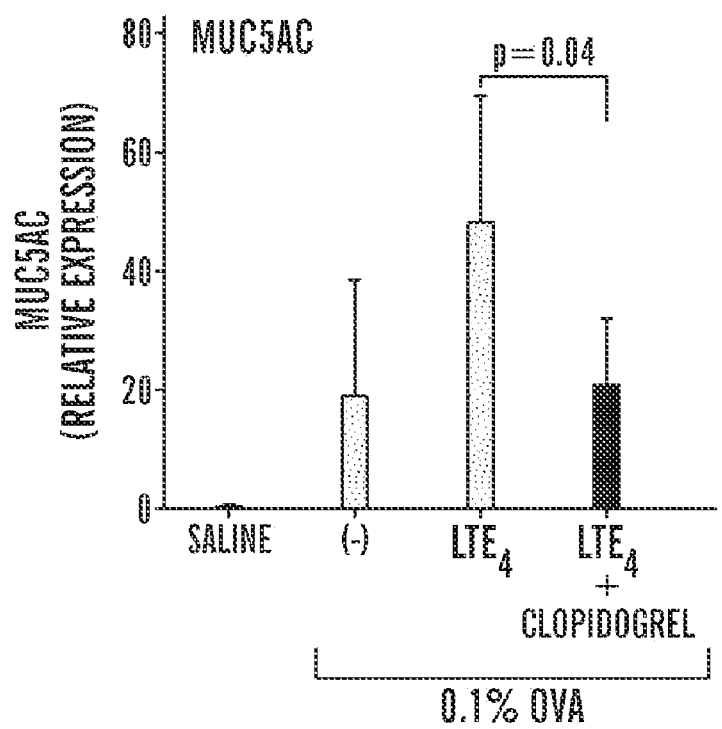

The Amplifying Effect of $LTE_4$ on Allergic Pulmonary Inflammation Depends on $P2Y_{12}$ Receptors To determine whether $P2Y_{12}$ receptors accounted for the $LTE_4$-mediated augmentation of pulmonary inflammation, sensitized mice were treated with clopidogrel, an antithrombotic agent that is converted in vivo to an active metabolite that covalently binds to $P2Y_{12}$ receptors and inhibits their function by partitioning them from lipid rafts (Savi, P., et al. 2006. *Proc. Natl. Acad. Sci. USA*. 103:11069-11074). Drug treatment began 2 days before the first administration of LTs to allow conversion of the prodrug. A separate cohort of mice were maintained without clopidogrel treatment as a control group. Both cohorts were challenged with low-dose OVA with or without additional $LTE_4$. The mice treated with clopidogrel showed complete lack of $LTE_4$-induced potentiation of both inflammation and goblet cell metaplasia (FIG. 5A, FIG. 5B). To determine the effect of $P2Y_{12}$ receptor blockade on the induced expression of mRNAs encoding proteins involved in goblet cell metaplasia, real-time PCR was used to analyze the lungs of the mice for the expression of IL-13 and the goblet cell-associated glycoprotein, MUC5AC. $LTE_4$ tended to increase the expression of both transcripts, while clopidogrel treatment substantially suppressed the expression of both (FIG. 5C). There was no detectable induction of IL-4 or IL-5 transcripts (data not shown).

Figure 4A:
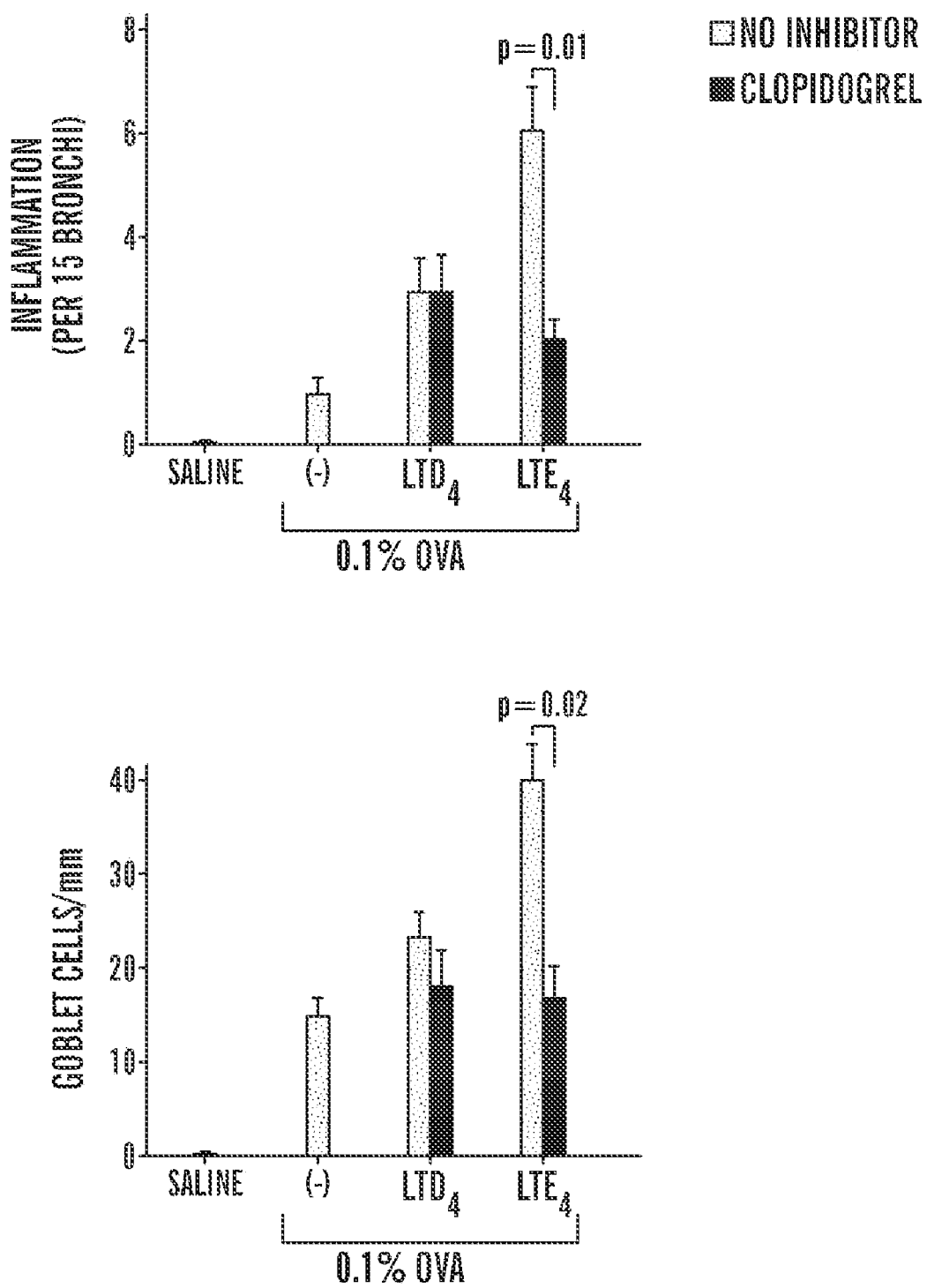
FIG. 4. Role of P2Y12 receptors on potentiation of pulmonary inflammation by LTE4. 4A. Bronchovascular inflammation (top) and goblet cell metaplasia in sensitized mice challenged with low-dose OVA with or without the prior administration of LTD4 or LTE4 (2.2 nmol) 12 h before each challenge. Clopidogrel (500 µg/ml) was added to the drinking water of the indicated groups of mice for 72 h before the first intranasal dose of LTs, and was maintained throughout the treatment. Results are mean±SEM from at least 9 mice in each group. The experiments were repeated three times with similar results. 4B. PAS stains (left column) from representative mice in the indicated groups showing the effect of clopidigrel on goblet cell metaplasia. Higher magnification images of H & E stains (right) from the same animals showing cellular characteristics of the bronchovascular infiltrates. 4C. Effect of clopidogrel administration on the steady-state expression of IL-13 and MUC5AC mRNA as determined by real-time PCR of whole lung RNA extracted 24 h after the last OVA challenge of the indicated groups. Data are mean±SEM from 4-5 mice/group from a single experiment. Results in a second experiment were similar 4D-4F. Male and female C57BL/6 p2ry12$^{-/-}$ mice and age and sex-matched controls were sensitized and challenged with 0.1% aerosolized OVA on three consecutive days with or without intranasal LTE4 12 h before each challenge. 4D. Total cell numbers (top), percentages of eosinophils (middle), and total numbers of eosinophils in BAL fluid recovered 24 h after the last challenge with OVA. 4E. Goblet cell metaplasia (top) and representative PAS stains (bottom) from wild-type and p2ry12$^{-/-}$ mice subjected to the same protocol. 4E. Inflammation scores from the same mice. Data in 4D-4F are from 4 mice per group. Results in a second experiment were similar 4G. BALB/c Cysltr1/Cysltr2$^{-/-}$ mice and age-matched WT controls were subjected to the same protocol as the p2ry12$^{-/-}$ mice. Total cell numbers (top), percentages of eosinophils (middle), and total numbers of eosinophils in BAL fluid recovered 24 h after the last challenge with OVA. Results are from 6 mice per group. Three experiments were performed with similar results. 4H. Goblet cell numbers (top) and representative PAS stains (bottom). 4I. Quantitative assessment of bronchovascular inflammation as determined by H & E stains. Results are from 6 mice/group.
Figure 4B:
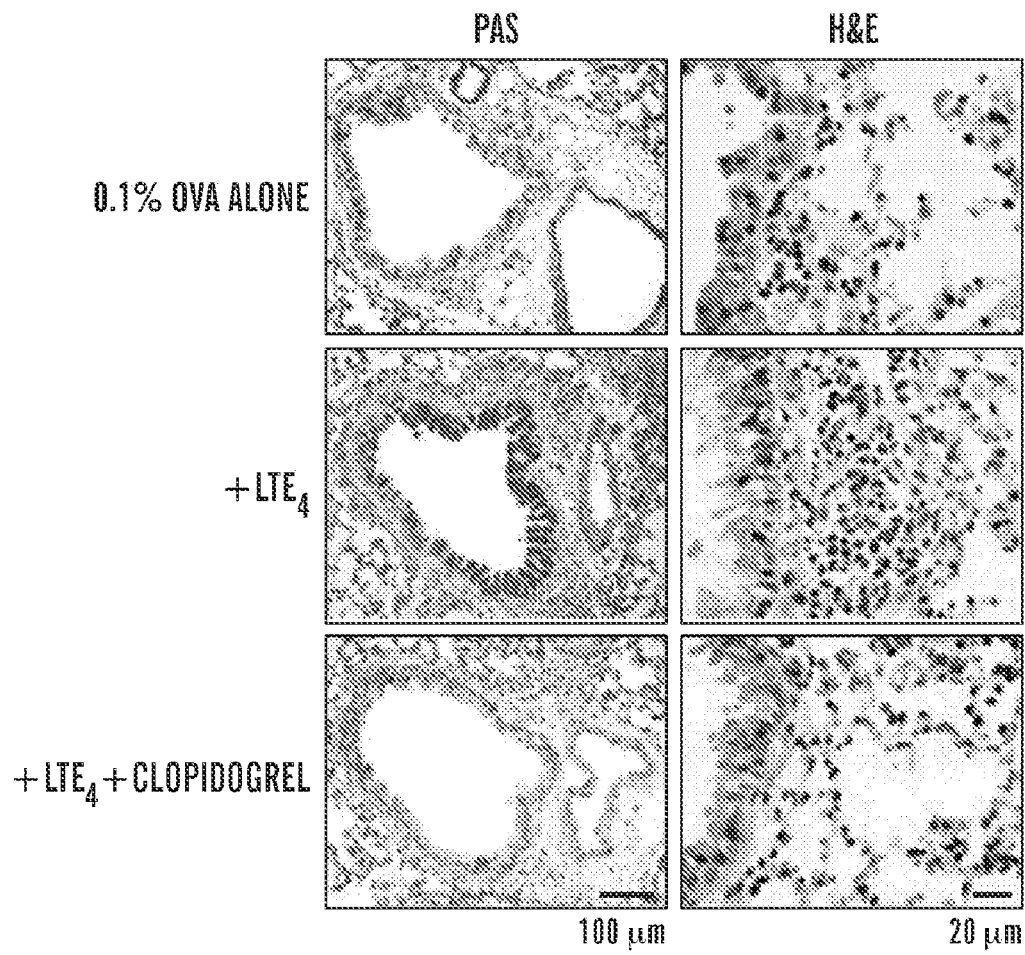
Figure 4C:
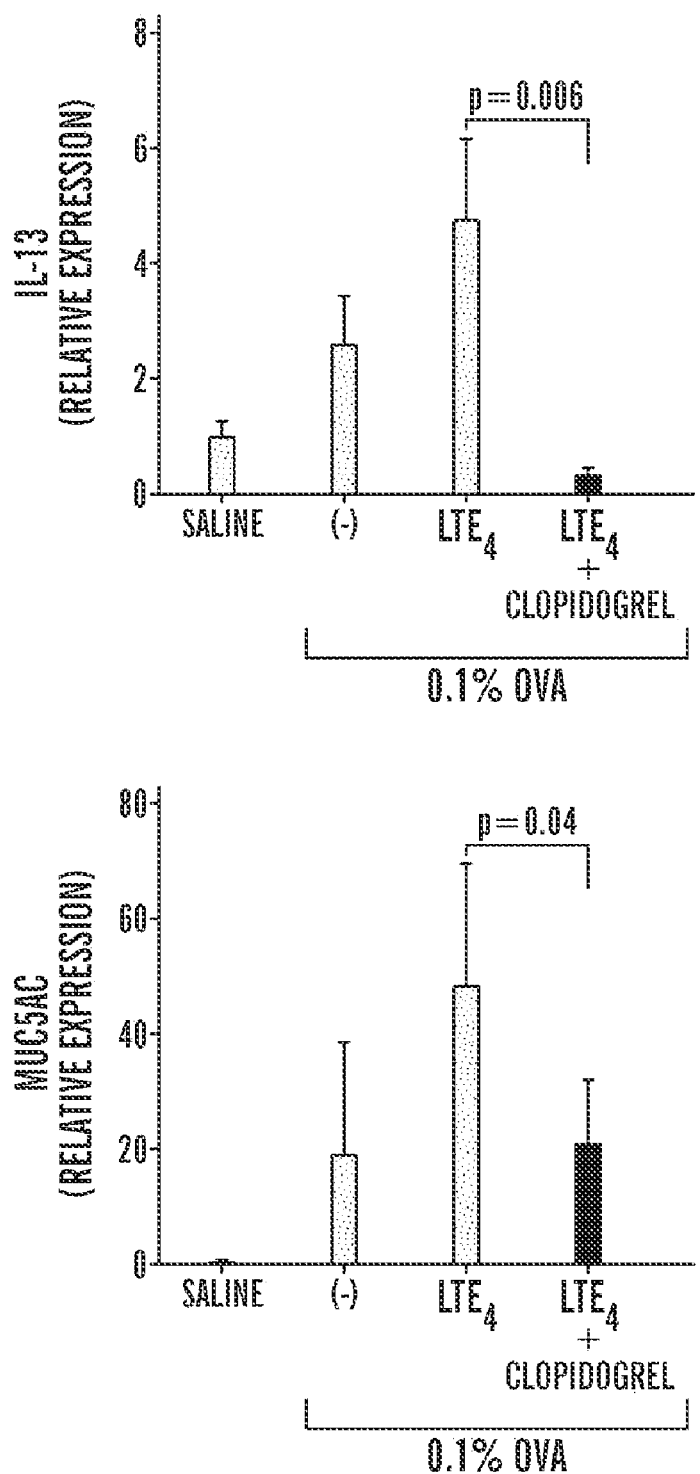
Figure 4D:
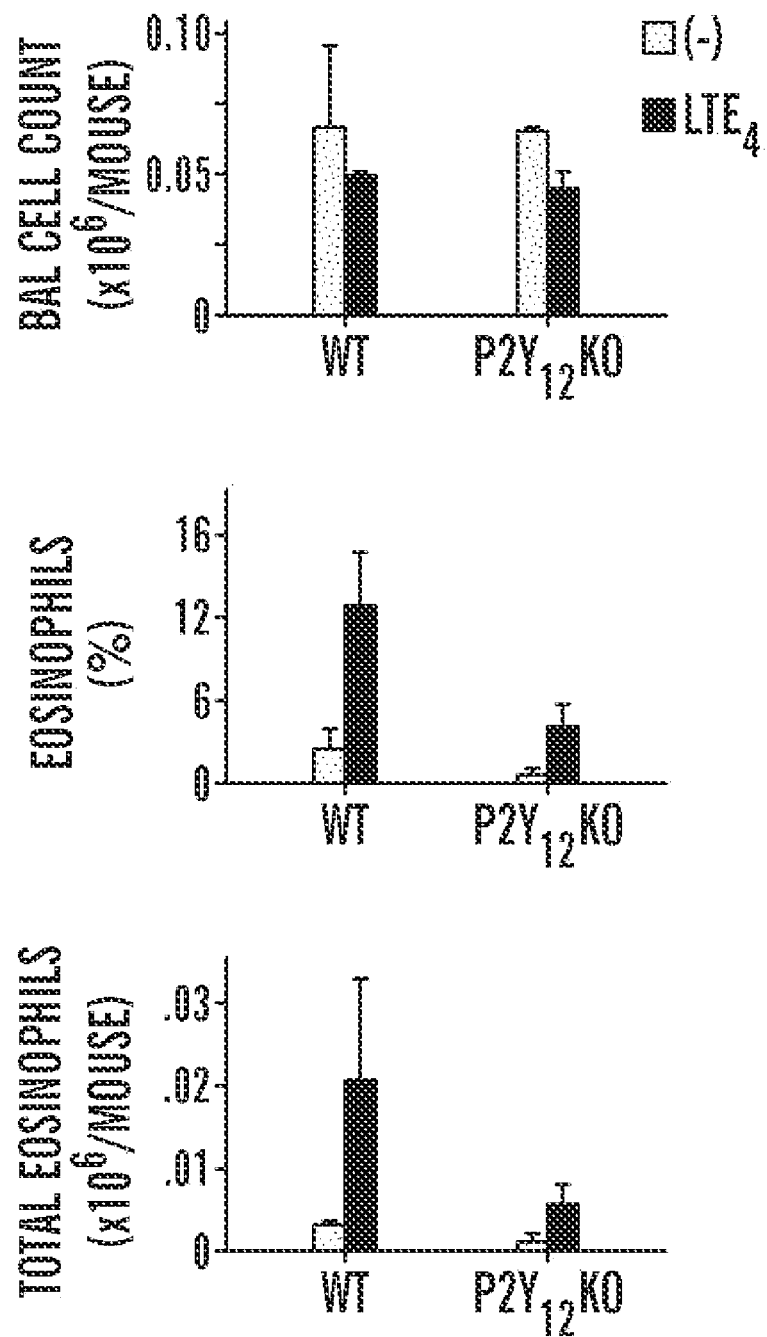
Figure 4E:
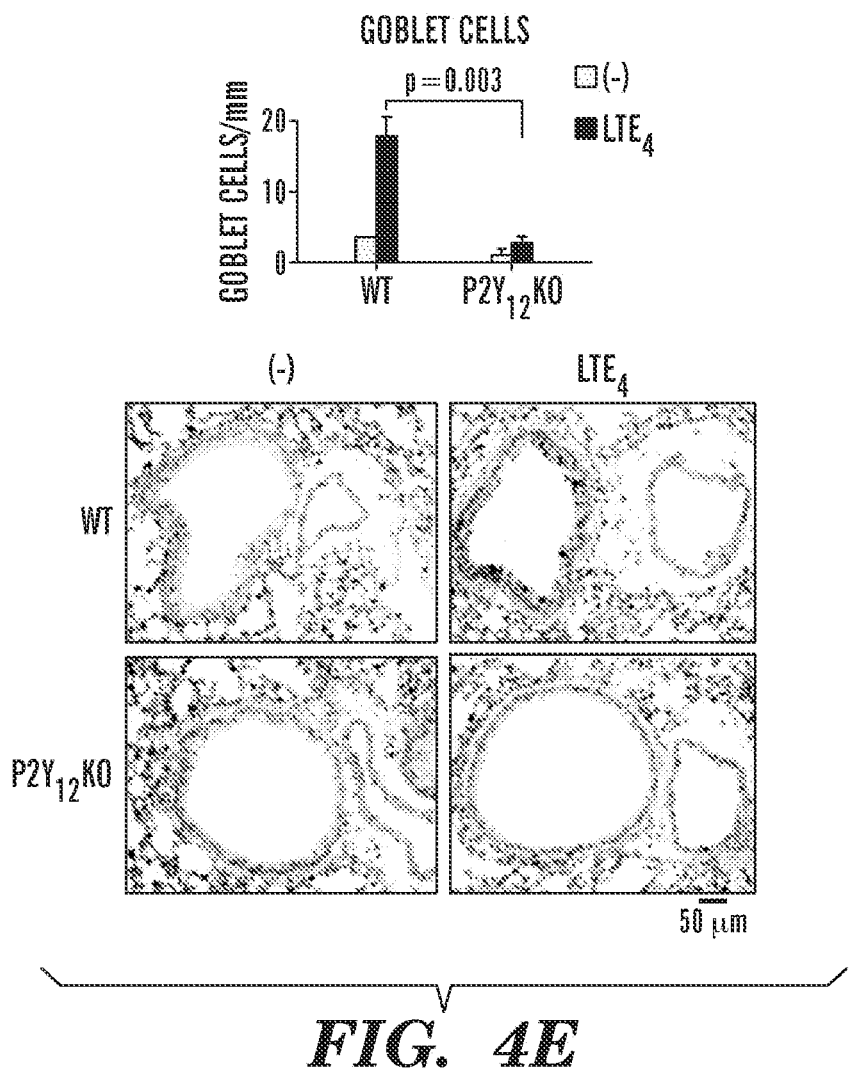
Figure 4F:
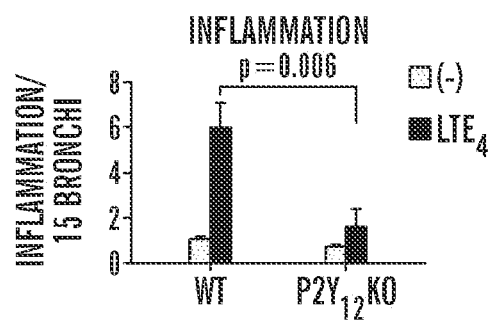
Figure 4G:
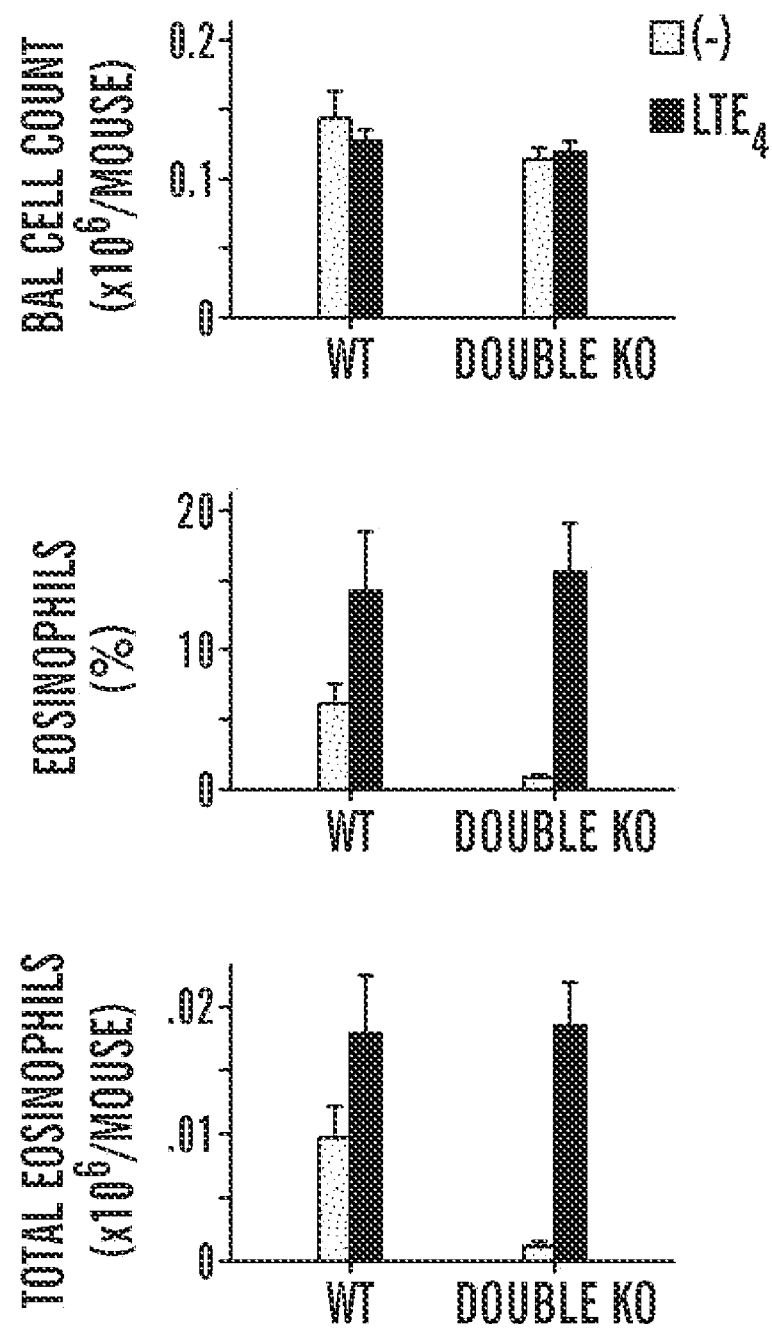

Because pharmacologic antagonists can act in an off-target manner, it was sought to determine the receptor(s) required to mediate the effect of $LTE_4$ in the lungs of allergen sensitized and challenged mice using a molecular approach. First, the ability of $LTE_4$ to amplify pulmonary inflammation was studied in OVA sensitized and challenged C57BL/6 mice lacking $P2Y_{12}$ receptors (p2ry12$^{-/-}$ mice) (Andre, P., et al. (2003) *J. Clin. Invest.* 112:398-406) along with age and sex-matched C57BL/6 controls. Although cellular infiltration into the lung and BAL fluid was less pronounced in the C57BL/6 mice than in the BALB/c mice, $LTE_4$ potentiated BAL fluid eosinophilia (FIG. 4D), goblet cell metaplasia (FIG. 4E) and bronchovascular infiltration (FIG. 4F) in the WT controls, all of which were severely blunted in the p2ry12$^{-/-}$ mice (FIG. 4D-F). To determine whether classical GPCRs for cys-LTs were also required for the $LTE_4$ effects, BALB/c mice lacking both $CysLT_1R$ and $CysLT_2R$ (Cysltr1/Cysltr2$^{-/-}$ mice) (Maekawa, A., et al. (2008) *Proc. Natl. Acad. Sci. U.S.A.* 105:16695-16700) were also studied.

Figure 4H:
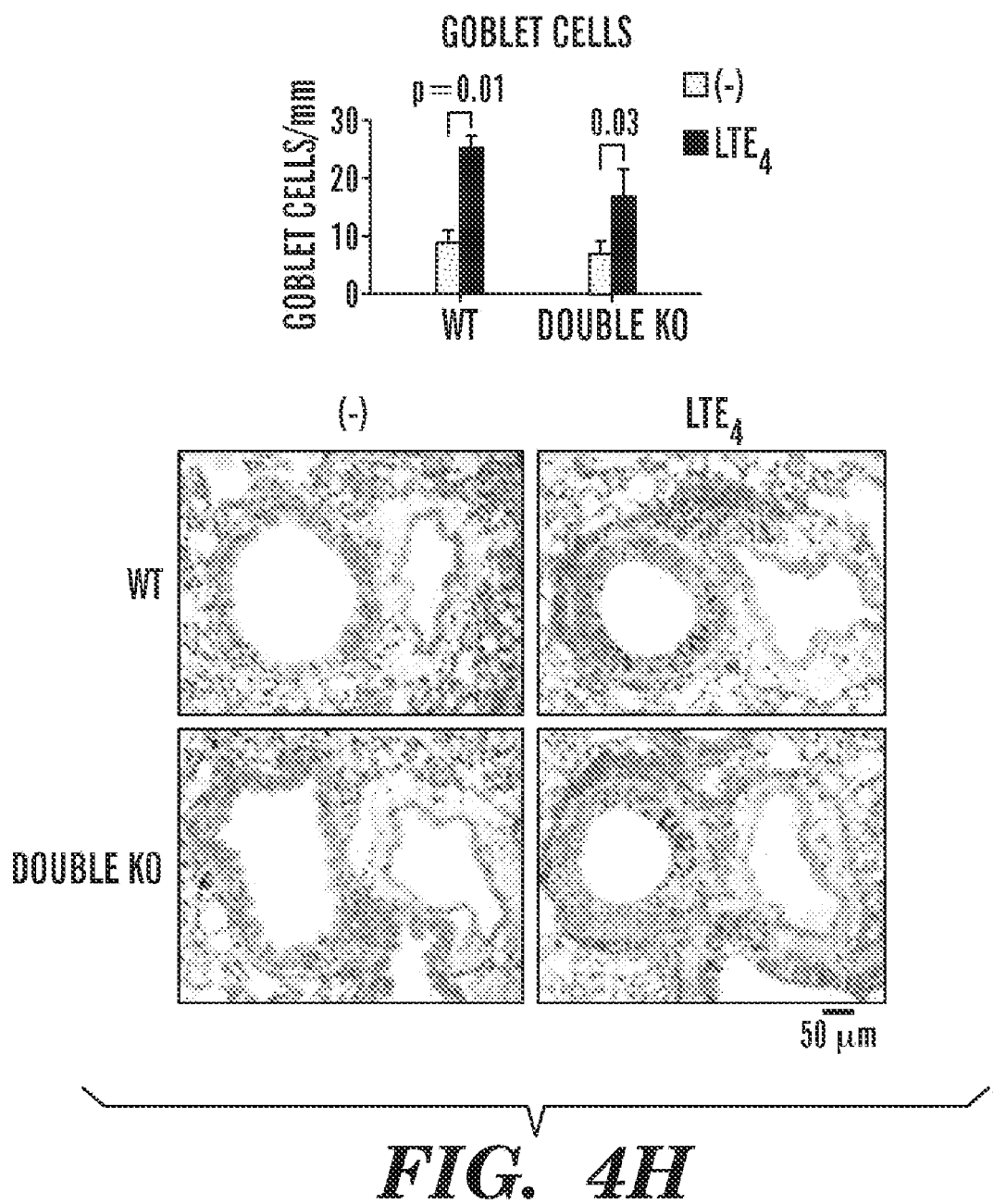
Figure 4I:
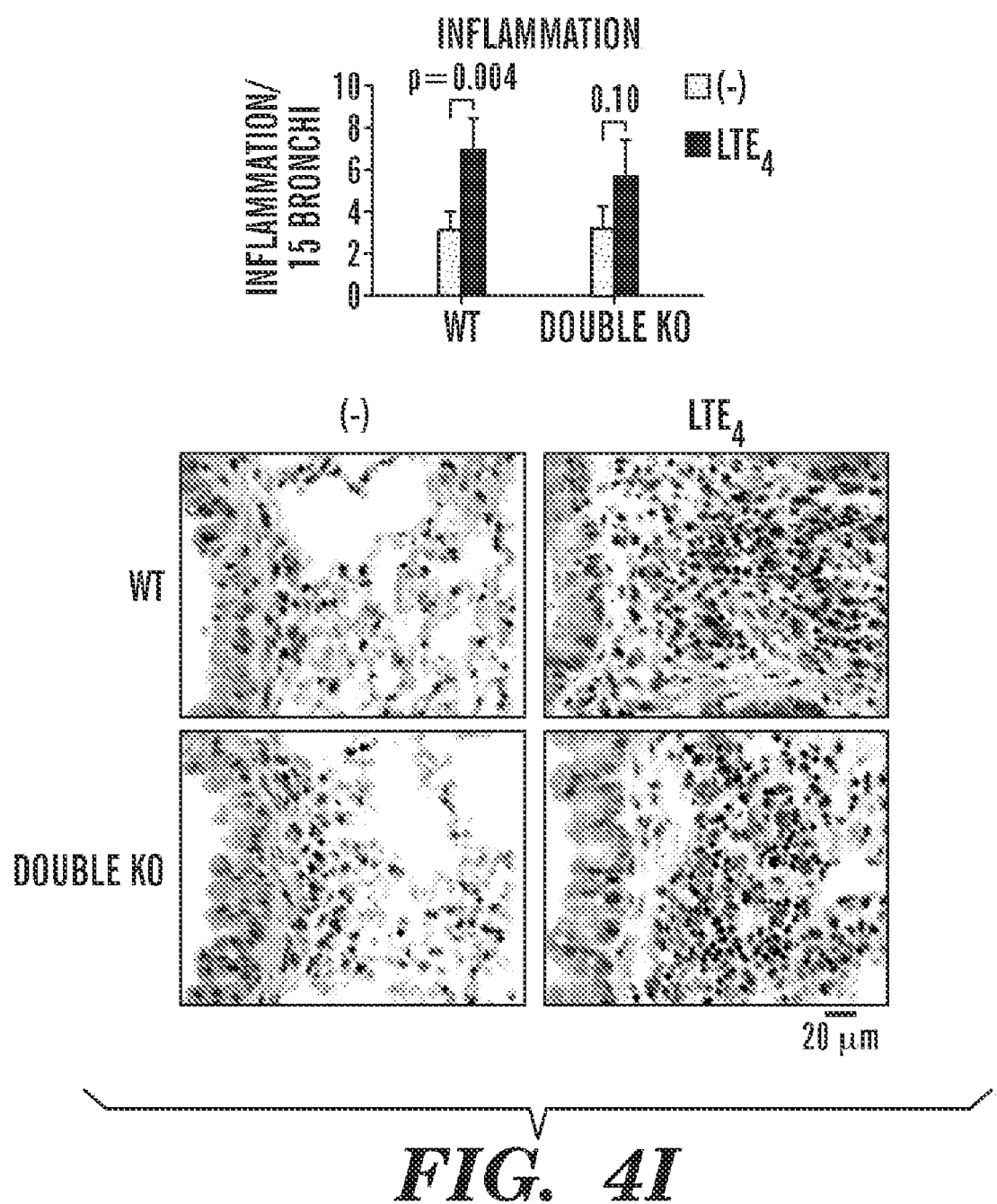

All animals were sensitized and challenged with low-dose OVA, and half were treated with exogenous $LTE_4$. The potentiation of OVA-induced BAL fluid eosinophilia (FIG. 4G), goblet cell metaplasia (FIG. 4H) and inflammation (FIG. 4I) by LTE4 were completely intact in the Cysltr1/Cysltr2$^{-/-}$ mice, indicating that $LTE_4$ was working independently of the known GPCRs for cys-LTs. Thus, the intrapulmonary actions of $LTE_4$ in vivo require $P2Y_{12}$ receptors, but not classical cys-LT-reactive GPCRs.

Blockade of P2Y12 Receptors Blunts Pulmonary Inflammation Induced by House Dust Mite Antigen.

Figure 7A:
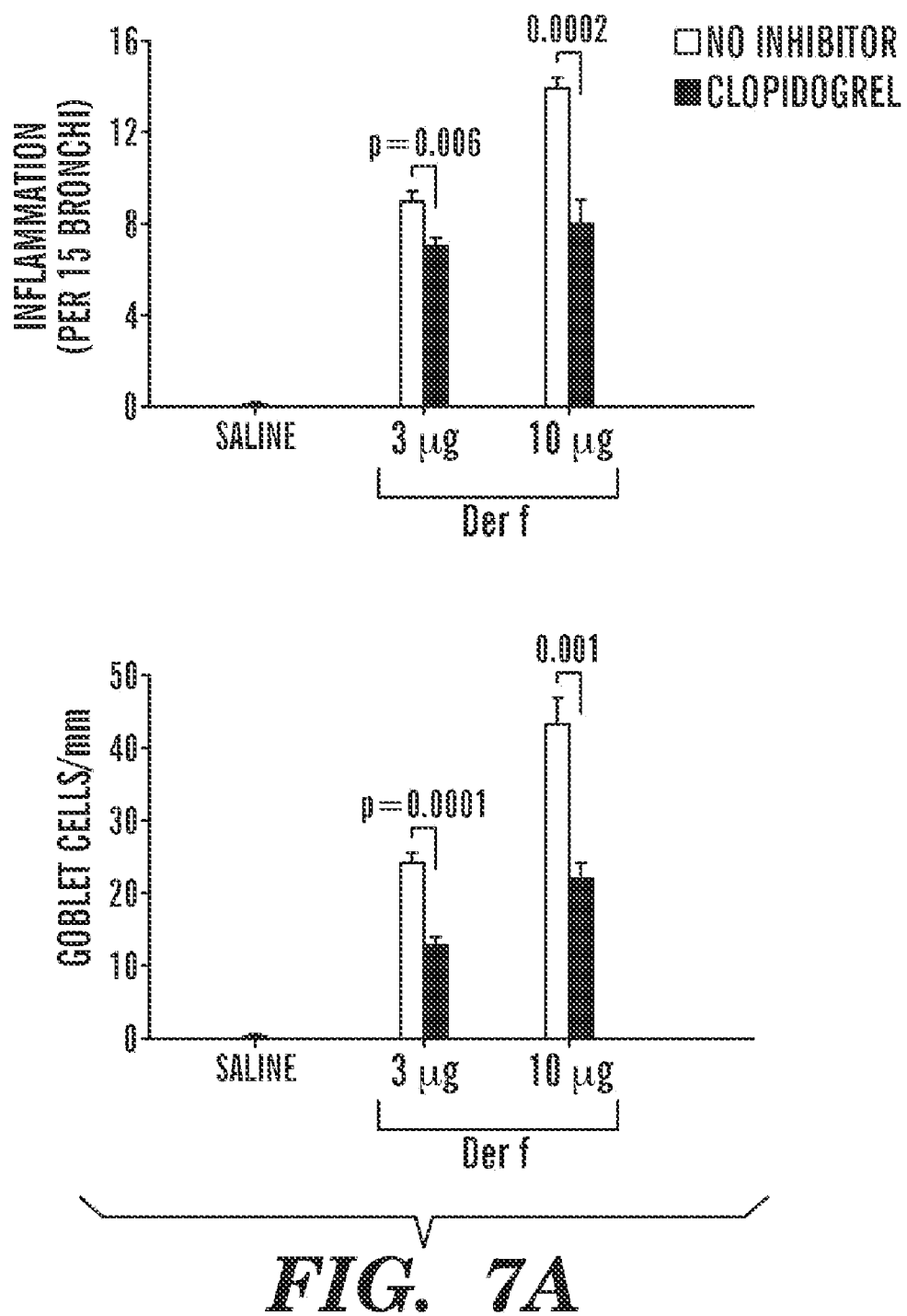
FIG. 7. Role of P2Y$_{12}$ receptors in inflammation mediated by dust mite allergen. C57BL/6 mice were treated intranasally with the indicated dose of *Dermatophagoides farinae* (Der f) extract twice weekly for 3 weeks. Animals were euthanized 24 h after the last dose. 7A. Effect of clopidogrel treatment on bronchovascular inflammation and goblet cell metaplasia in C57BL/6 mice subjected to intranasal challenge with the indicated doses of an extract from the house dust mite. Results are the mean±SEM from 5 mice/group. The experiment was repeated three times with similar results. 7B. Representative PAS stains of the lungs from mice in the indicated groups.
Figure 7B:
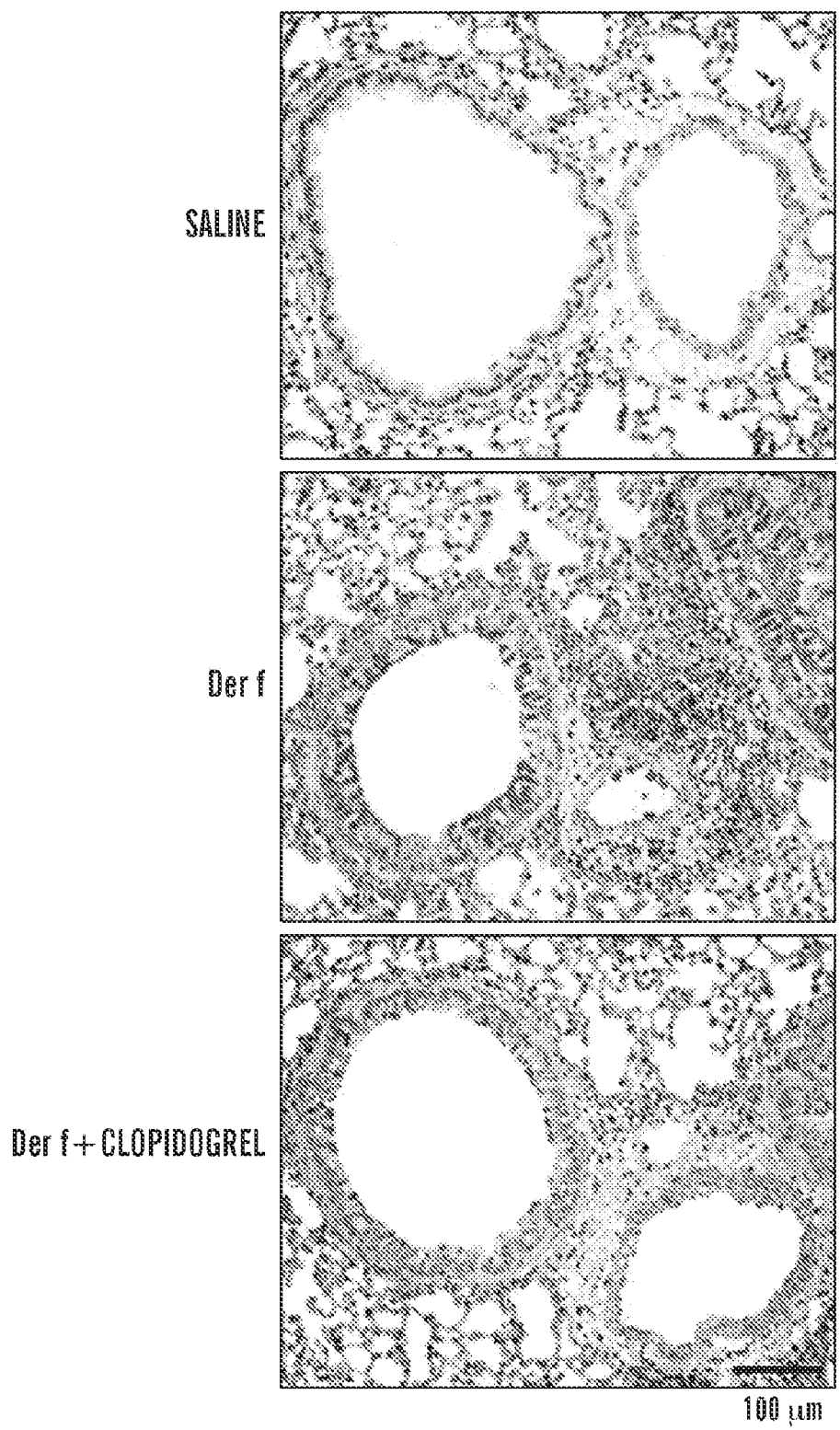
Figure 8:
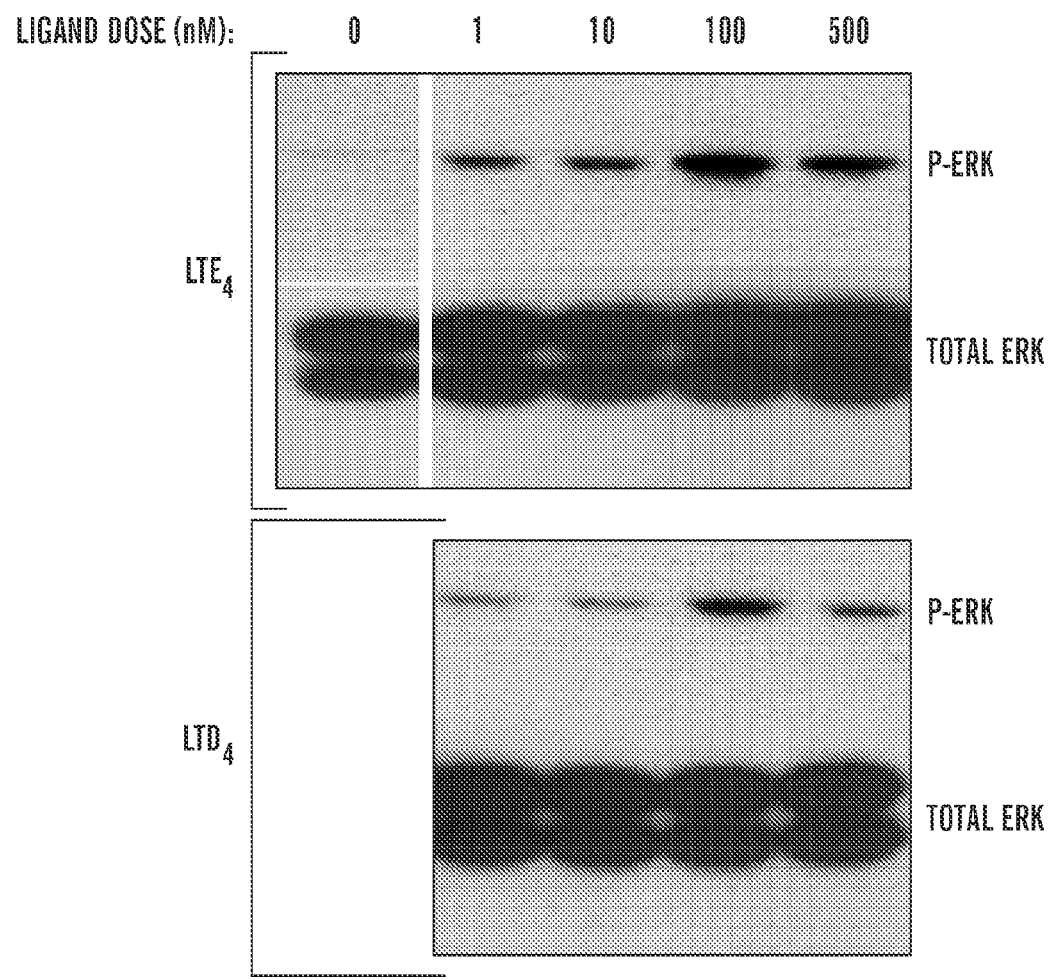

To determine whether pharmacologic blockade of $P2Y_{12}$ receptors altered pulmonary inflammatory responses in a more physiologic model of pulmonary inflammation, C57BL/6 mice were administered an extract of house dust mite *Dermatophagoides farinea* (Der f) intranasally twice weekly for three weeks, with or without clopidogrel treatment. Two different doses of Der f were used to elicit moderate (at 3 μg) and severe (at 10 μg) inflammation, respectively. At both antigen doses, the mice treated with clopidogrel showed ~75% attenuation of BAL fluid eosinophilia (not shown), as well as significant reductions in pulmonary inflammation, and goblet cell metaplasia compared to the cohort that did not receive clopidogrel (FIG. 7A, FIG. 7B).

Example 5

Figure 6A:
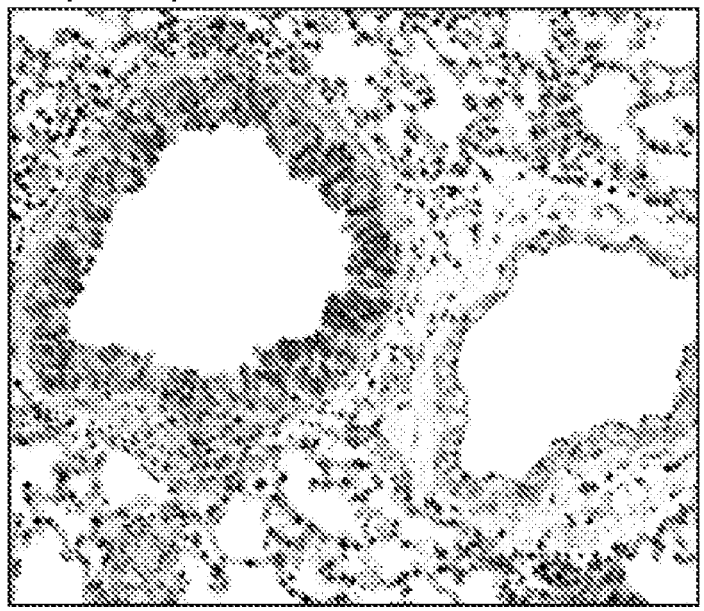
FIG. 6. Platelet dependence of the LTE4 effect on bronchial inflammation and goblet cell metaplasia. Sensitized mice were treated intravenously with 50 µg (~2 µg/g body weight) of a monoclonal rat IgG directed against mouse CD42b (GPIbα) or an equal amount of isotype control (both from Cemfret Analytics) 48 h before the first dose of LTE4. Each antibody (Ab) was diluted in 50 µl of sterile saline. The depletion of platelets was confirmed by automated counting, and some mice were treated with clopidogrel. 6A. PAS stains of the lungs of representative mice treated with isotype control (top) or with an anti-CD42 platelet-depleting antibody (bottom). 6B. Inflammation (top) and goblet cell metaplasia (bottom) in the lungs of mice treated with the indicated LT and antibody. A cohort of mice was treated with clopidogrel as indicated. Results in 6B are from a single experiment with 5 mice per group. A second experiment with an equal number of mice showed similar results. 6C. Cytofluorographic detection of surface expression of CD62P (P-selectin) by platelets stimulated for 10 min with ADP (100 µM) or LTE4 (1 µM). Percentages of CD61-positive platelets expressing CD62P are displayed in the right upper quadrants. Results are from a single experiment performed three times on different donors.
Figure 6A:
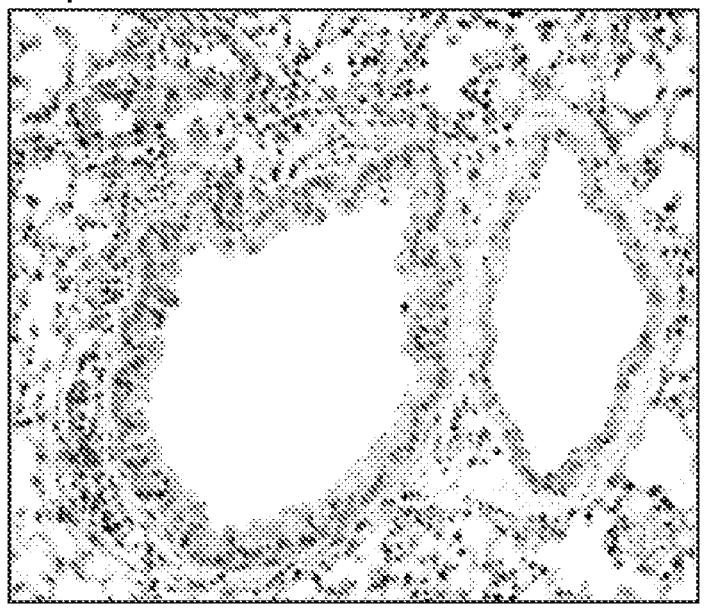
Figure 6B:
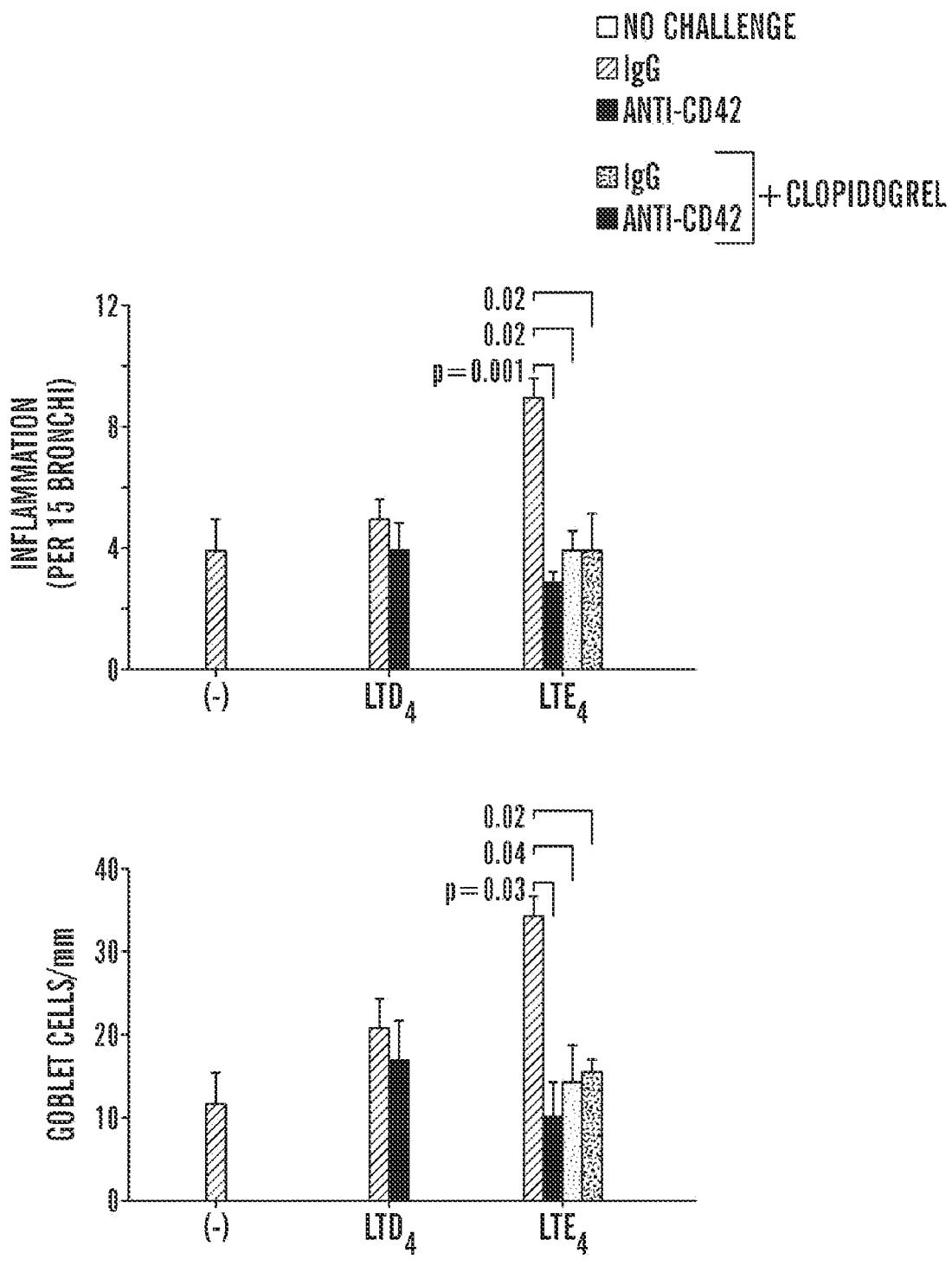
Figure 6C:
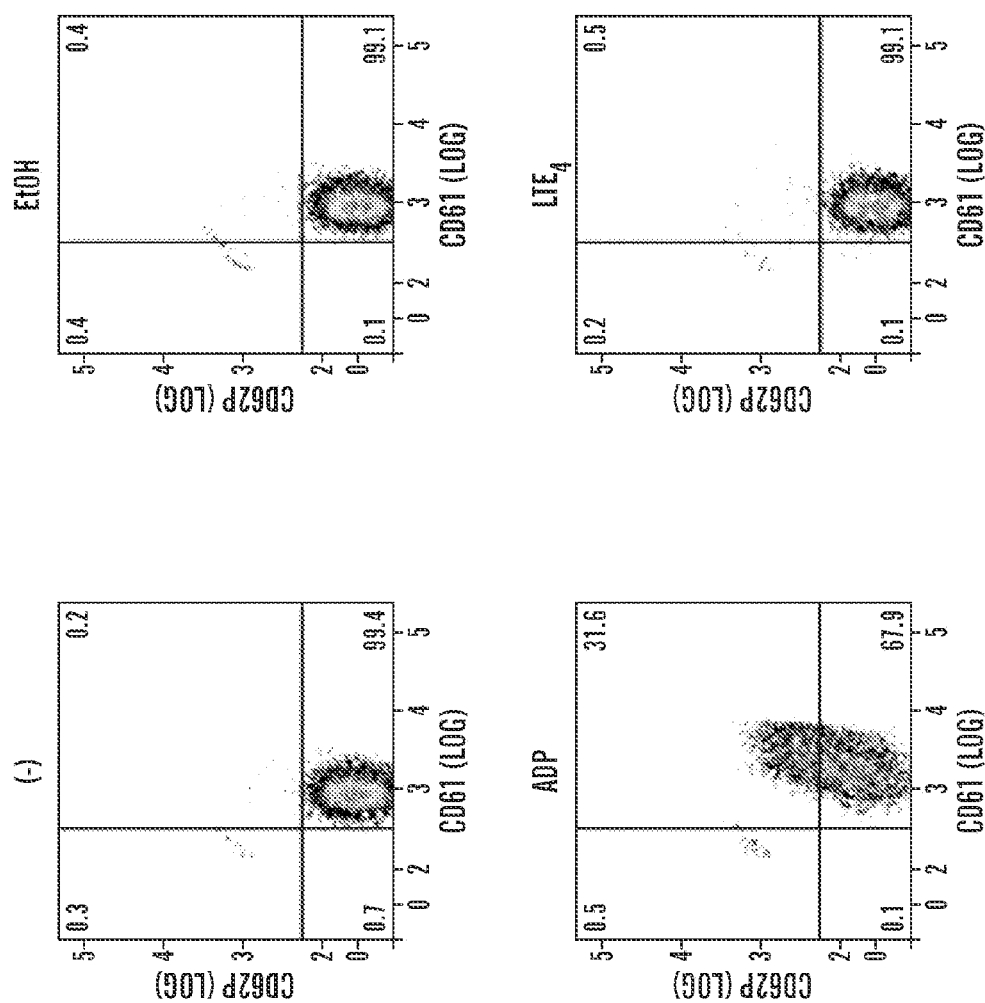

$LTE_4/P2Y_{12}$ Receptor-Mediated Amplification of Pulmonary Inflammation Requires Platelets Platelets accumulate in the lungs of asthmatic individuals (Jeffery, P. K., et al. 1989. *Am. Rev. Respir. Dis.* 140:1745-1753), and are also recruited to the lungs of ovalbumin sensitized and challenged mice by an IgE-dependent mechanism (Pitchford, S. C., et al. 2008. *Am. J. Respir. Crit. Care Med.* 177:604-612). Since $P2Y_{12}$ receptors are essential for normal platelet activation in vivo (Andre, P., et al. 2003. *J. Clin. Invest.* 112:398-406), experiments were designed to determine whether platelets were required for the response of sensitized challenged mice to exogenous $LTE_4$. Platelets were depleted in sensitized mice by the intravenous injection of a rat monoclonal Ab against mouse CD42b (GPIbα) (Neiswandt, B., et al. 2000 *Blood.* 96:2520-2527) or with an isotype-matched control IgG 48 h prior to the first administration of $LTD_4$ or $LTE_4$. Treatment with the anti-CD42b Ab depleted platelets virtually completely (99% depletion, not shown) at the time of the first dose of LT. Platelet depletion resulted in a complete loss of the $LTE_4$-mediated potentiation of airway eosinophilia, inflammation, and goblet cell metaplasia (FIGS. 6A, 6B). The effect of platelet depletion was identical to the treatment of the mice with clopidogrel, and the two treatments were not additive (FIG. 6B). Platelet depletion, like clopidogrel treatment, sharply reduced the $LTE_4$-mediated expression of mRNA encoding IL-13 and MUC5AC (not shown). To determine whether $LTE_4$ alone induced platelet activation (leading to ADP release with potential resultant autocrine stimulation of P2Y12 receptors), human blood platelets were stimulated with $LTE_4$ (1 μM) or with ADP (100 μM), and degranulation was assessed by cytofluorographic detection of P-selectin (CD62P). As expected, ADP elicited CD62P expression, but no CD62P expression was detected in response to stimulation with $LTE_4$ (FIG. 6C).

The involvement of cys-LTs in the pathobiology of asthma is proven by the fact that 5-LO inhibitors (Israel, E., et al. 1996 *JAMA* 275:931-936) and $CysLT_1R$ antagonists (Dahlen, S. E. et al. 2002. *Am. J. Respir. Crit. Care Med.* 165:9-14) show clinical efficacy, particularly in the AERD variant associated with marked cys-LT overproduction. Although never directly compared, there is general consensus that the 5-LO antagonist zileuton shows superior clinical efficacy to $CysLT_1R$ antagonists, even though the former only blocks ~50% of cys-LT generation in vivo (Israel, E., et al. 1996 *JAMA* 275:931-936). The cloning and functional characterizations of the $CysLT_1R$ and $CysLT_2R$ explained the pharmacology of $LTC_4$ and $LTD_4$ predicted from studies of contractile tissues (Lynch, K. R., et al. 1999. *Nature.* 399:789-793; Heise, C. E., et al. 2000. *J. Biol. Chem.* 275:30531-30536). Surprisingly, however, neither GPCR showed significant binding or reactivity to $LTE_4$, given the plethora of data in human and animal studies that indicated the unique characteristics of this stable ligand relative to its short-lived precursors (Lee, T. H., et al. 1984. *Proc. Natl. Acad. Sci. USA.* 81:4922-4925; Christie, P. E., et al. 1992. *Am. Rev. Respir. Dis.* 146:1506-1510; Laitinen, L. A., et al. 1993. *Lancet.* 341:989; Gauvreau, G. M., et al. 2001. *Am. J. Respir. Crit. Care Med.* 164:1495-1500; Christie, P. E., et al. 1993. *Eur. Respir. J.* 6:1468-1473). It was previously demonstrated that hMCs expressed a broad range of P2Y receptors for adenine nucleotides, including the ADP-reactive $P2Y_{12}$ receptor (Feng, C., et al. 2004. *J. Immunol.* 173:7539-7547). In a recent study, strong pharmacologic evidence for the existence of an $LTE_4$-reactive "$CysLT_3R$" expressed by the human LAD2 MC line and by primary hMCs (Paruchuri, S., et al. 2008. *J. Biol. Chem.* 283:16477-16487) was shown. Since $LTE_4$ was previously identified by an in silico model as a potential surrogate ligand for the $P2Y_{12}$ receptor (Nonaka, Y., et al. 2005. *Biochem. Biophys. Res. Commun.* 337:281-288), and the experiments described herein show that the $P2Y_{12}$ receptor is a bona fide $LTE_4$-reactive $CysLT_3R$.

Unlike most members of the P2Y receptor class, native $P2Y_{12}$ receptors do not couple to Gαq proteins or activate calcium flux; instead, they induce signaling through pertussis toxin (PTX)-sensitive Gαi2 proteins and induce ERK phosphorylation in platelets stimulated with ADP (Lova, P., S. et al. 2002. *J. Biol. Chem.* 277:12009-12015). It was thus not surprising that CHO cells expressing $P2Y_{12}$ receptors failed to flux calcium in response to cys-LTs (FIG. 1A), or that blockade of $P2Y_{12}$ receptors on LAD2 cells with 2-MesAMP failed to alter cys-LT-mediated calcium flux (FIG. 2A), which was abrogated by MK571. However, the fact that heterologously expressed $P2Y_{12}$ receptors responded to $LTE_4$ and $LTD_4$ with PTX-sensitive ERK activation (FIGS. 1B, 1C) is consistent with their function as true $CysLT_3Rs$. Without wishing to be bound by theory, the observation that cys-LT-induced ERK activation in the transfectants were resistant to MK571 (FIG. 1C) implies that $P2Y_{12}$ receptors contribute an element of cys-LT-driven pathobiology that may resist conventional $CysLT_1R$ antagonists. Without wishing to be bound by theory, the fact that $P2Y_{12}$ receptors bind $LTE_4$ with a log-fold higher affinity than does $CysLT_1R$ or $CysLT_2R$ implies that its functions are especially relevant to pathologic situations where $LTE_4$ is abundant due to the relative stability of this ligand.

In a previous study, $LTE_4$ had exhibited unanticipated potency for inducing ERK activation, and the generation of MIP-1β and COX-2-dependent $PGD_2$ by LAD2 cells (Paruchuri, S., et al. 2008. *J. Biol. Chem.* 283:16477-16487). Since both ERK and calcium-dependent transcriptional events are essential for MC activation, it was sought to determine the potential contribution of $P2Y_{12}$ receptors to the activation responses of LAD2 cells to $LTE_4$, and contrast these responses to those elicited by $LTD_4$, the most potent $CysLT_1R$ ligand. Although ineffective for blocking cys-LT-induced calcium flux, 2-MesAMP was efficacious for blocking the $LTE_4$-mediated increment in MIP-1β production (FIG. 2B), and also reduced the response to the higher concentrations of $LTD_4$, reflecting actions of the latter ligand at $P2Y_{12}$ receptors as supported by its actions as an agonist for ERK activation. MK571 suppressed the response to both ligands (likely reflecting the requirement for calcium flux for chemokine generation), and was additive with 2-MesAMP for the suppression of the response to $LTD_4$. The shRNA-mediated knockdowns of $CysLT_1R$ and $P2Y_{12}$ receptors revealed strong dependence of $LTD_4$-mediated activation on $CysLT_1R$, whereas $LTE_4$-mediated responses were clearly $P2Y_{12}$ receptor-dependent. While there is striking segregation of the receptor requirements for these two related ligands on the same cell, the ability of $LTE_4$ to "crossover" and induce some calcium signaling through $CysLT_1R$ may permit some complementarities between $CysLT_1R$ (via Gαq proteins and calcium-induced pathways) and $P2Y_{12}$ (via Gαi proteins), particularly for chemokine generation. This is analogous to the cooperation by Gαq-linked $P2Y_{12}$ receptors with $P2Y_{12}$ receptors in regulating ADP responses of platelets (Lova, P., et al. 2002. J. Biol. Chem. 277:12009-12015). The P2Y12-dependent activation of LAD2 cells does not likely reflect autocrine effects of released ADP, since it was resistant to treatment of the cells with the ectonucleotidase apyrase as shown and/or described herein. Surprisingly, while $P2Y_{12}$ receptors were essential for competition between $LTE_4$ with ADP for binding to membranes of LAD2 cells, they were not involved in the direct low-affinity binding of $[H^3]LTE_4$ to these same membranes. Additionally, $LTE_4$ could not compete for binding to $P2Y_{12}$ receptors expressed in isolation on COS-7 cells. Without wishing to be bound by theory, the observation that $P2Y_{12}$ receptors do not directly bind $LTE_4$ despite their essential nature imply that they are components of a complex with another $LTE_4$-reactive GPCR, perhaps with the putative "CysLTER" reported in the mouse skin (Maekawa, A., et al. (2008) *Proc. Natl. Acad. Sci. U.S.A.* 105:16695-16700.). The fact that $P2Y_{12}$ receptors are required for $LTE_4$ to activate transfected CHO cells and LAD2 cells, and for competition between $LTE_4$ and ADP for binding to LAD2 cells, and that knockdown of $P2Y_{12}$ receptors did not reduce direct binding of radiolabeled $LTE_4$ are all consistent with this thesis. Precedents for such complexes on MCs include $CysLT_1R$ and $CysLT_2R$ heterodimers (Jiang, Y., et al. (2007) *Blood.* 110:3263-3270), and a functional requirement of $CysLT_1R$ for the uridine diphosphate-reactive $P2Y_6$ receptor (Jiang, Y., et al. (2009) *J. Immunol.* 182:1129-1137). Without wishing to be bound by theory, the data indicate that presence of $P2Y_{12}$ is required for signaling and activation by $LTE_4$ in a cell-specific context.

The fact that $LTE_4$, but not $LTD_4$, induces bronchial eosinophilia when administered by inhalation to the airways of asthmatic individuals (Christie, P. E., et al. 1992. *Am. Rev. Respir. Dis.* 146:1506-1510; Laitinen, L. A., et al. 1993. *Lancet.* 341:989) argued for the presence of an $LTE_4$-reactive receptor in inflamed lung. In the model described herein, designed to study potentiation of bronchial inflammation in sensitized mice, it was found that $LTE_4$ exceeded the potency of $LTD_4$ for potentiating BAL fluid eosinophilia (FIG. 3A), cellular infiltration of the bronchovascular bundles (FIGS. 3B, 3C), and goblet cell metaplasia (FIGS. 3D, 3E). Thus, LTE4 exceeds the efficacy of LTD4 for potentiating bronchial inflammation in both mouse and man, a pattern not explicable by the known properties of CysLT1R or CysLT2R.

Several pieces of evidence link these LTE4-mediated responses in mice to the $P2Y_{12}$ receptor. First, the $LTE_4$-dependent increment in inflammatory signatures was completely intact in mice lacking both $CysLT_1R$ and $CysLT_2R$ (FIG. 4). Second, treatment of the mice with a highly potent, selective antagonist of the $P2Y_{12}$ receptor, clopidogrel, completely eliminated the response to histologic response to $LTE_4$ (FIGS. 5A, 5B). Lastly, the ability of $LTE_4$ to potentiate mucosal inflammation and goblet cell metaplasia was nearly completely abrogated in the absence of P2Y12 receptors (FIG. 4D-F). Thus, $LTE_4$ requires $P2Y_{12}$ receptors, but not the classical CysLTRs, to amplify the histologic signatures of allergen-induced pulmonary inflammation. In addition to P2Y12-dependent effects of $LTE_4$, $LTD_4$ may initiate inhibitory signals through $CysLT_2R$ (Jiang, Y., et al. (2007) *Blood* 110:3263-3270.) or other yet-to-be-identified GPCRs that recognize $LTD_4$ but not $LTE_4$, The effects of clopidogrel in the model of airway disease induced by the natural allergen Der f without the use of exogenous $LTE_4$ supports the importance of the $P2Y_{12}$ pathway in the integrated biology of pulmonary inflammation (although this does not discriminate between effects mediated by $LTE_4$ from ADP). The blockade of the response by clopidogrel distinguishes the $P2Y_{12}$ receptor-dependent response of the lung to $LTE_4$ from the clopidogrel-resistant $LTE_4$ response in the skin (Maekawa, et al. (2008) *Proc. Natl. Acad. Sci. U.S.A.* 105:16695-16700). Thus it is likely that different receptors or receptor complexes mediate response to the stable ligand $LTE_4$ in distinct anatomic distributions. These striking inhibitory effects were associated with blockade of $LTE_4$-potentiated expression of IL-13, the Th2 cytokine most closely linked to the development of goblet cell metaplasia (Zhu, Z., et al. 1999. *J. Clin. Invest.* 103:779-788), and of MUC5AC, the major mucous glycoprotein that is controlled by IL-13 (FIG. 5C). Thus $P2Y_{12}$ receptors, and not the classical CysLTRs, mediate a powerful potentiating effect of $LTE_4$, amplifying the expression of genes that culminate in histologic signatures of asthma. The fact that $LTE_4$ exceeds the potency of $LTD_4$ may reflect the ability of the latter ligand to initiate inhibitory signals through $CysLT_2R$ (Jiang, Y., et al. 2007. *Blood.* 110: 3263-3270) or other yet-to-be-identified GPCRs not activated by $LTE_4$.

Activated platelets accumulate in the lungs of humans with asthma (Jeffery, P. K., et al. 1989. *Am. Rev. Respir. Dis.* 140:1745-1753) and allergen sensitized and challenged mice (Pitchford, S. C., et al. 2008. *Am. J. Respir. Crit. Care Med.*

177:604-612), and generate mediators (serotonin, thromboxane) that can potentiate airway inflammation. The essential nature of $P2Y_{12}$ receptors for normal platelet function (Andre, P., et al. 2003. *J. Clin. Invest.* 112:398-406) led us to examine the effect of platelet depletion on the response of sensitized challenged mice to exogenous $LTE_4$. Indeed, the response to $LTE_4$ was abrogated by platelet depletion (FIGS. 6A, 6B). It is noteworthy that $LTE_4$-mediated potentiation of contractile responses of both guinea pig and human airway smooth muscle was attributed to secondary generation of thromboxane, a major platelet-derived eicosanoid (Jacques, C. A., et al. 1991. *British J. Pharmacol.* 104:859-866). In retrospect, this may have reflected $P2Y_{12}$ receptor-dependent signaling on platelets (Jin, J., et al. 2002. *Blood.* 99:193-198), although a contribution from MC-derived $PGD_2$ also seems possible.

The findings described herein help to explain long-recognized but unexplained properties of $LTE_4$ in airway biology, and indicate a potential therapeutic application for $P2Y_{12}$ receptor antagonists to airway disease. This is especially relevant to AERD, which is associated with both high levels of $LTE_4$ in the urine and selective hyperresponsiveness to $LTE_4$ (Christie, P. E., et al. 1993. *Eur. Respir. J.* 6:1468-1473). Whether the requirement for platelets is direct or indirect is less clear. Without wishing to be bound by theory, the fact that $LTE_4$ did not induce platelet expression of CD62P (an activation marker used as a surrogate for ADP release) indicates that $LTE_4$ does not trigger an ADP-dependent autocrine loop initiated by $LTE_4$-mediated activation of another receptor. Since platelet activation involves complementary signaling both Gi and Gq protein-mediated pathways, and P2Y12 provides only the Gi-linked component, $LTE_4$ (and P2Y12) likely synergize in vivo with a second agonist lung to facilitate platelet functions in the lung. It is noteworthy that $LTE_4$-mediated potentiation of the contractile responses of both guinea pig and human airway smooth muscle is COX-dependent (Lee, T. H., et al. (1984) *Proc. Natl. Acad. Sci. USA.* 81:4922-4925; Christie, P. E., (1992) *Am. Rev. Respir. Dis.* 146:1506-1510), and was attributed to secondary generation of thromboxane, a major platelet-derived eicosanoid (Jacques, C. A., et al. (1991) *British J. Pharmacol.* 104:859-866). In retrospect, this finding may have reflected P2Y12 receptor-dependent signaling on platelets or other cell types. The fact that $LTE_4$ potentiated inflammation only in sensitized, challenged mice may reflect the previously described platelet-mediated pathway for leukocyte recruitment that depends on sensitization and IgE (Pitchford, S. C., et al (2008) *Am. J. Respir. Crit. Care Med.* 177:604-612). The complete lack of LTE4 reactivity in the face of platelet depletion argues against a role for MCs and other $P2Y_{12}$-bearing cell types, at least in this model.

Importantly, the fact that the effects of $LTE_4$ persisted in the absence of $CysLT_1R$ and $CysLT_2R$ implies that this pathway would be resistant to the available cys-LT receptor antagonists, all of which selectively block $CysLT_1R$. $CysLT_1R$. Without wishing to be bound by theory, it is speculated that simultaneous interference with the bronchoconstrictive effects of $LTD_4$ (via $CysLT_1R$) and with proinflammatory effects of $LTE_4$ (by $P2Y_{12}$), or more complete blockade of 5-LO, might improve clinical efficacy. This study furthermore highlights the functional significance of the structural relationship between the P2Y and cys-LT-reactive classes of GPCRs. It is noteworthy that treatment of mice with suramin, a general inhibitor of P2Y receptor signaling, dramatically inhibited allergen-induced pulmonary inflammation and AHR in a mouse model of asthma (Idzko, M., et al. 2007. *Nature Med.* 13:913-919). Moreover, the recent evidence for the involvement of cys-LTs in cardiovascular disease (Hakonarson, H., et al. JAMA 293:2245-2256) may also partly reflect the ability of $LTE_4$ to induce signaling in platelets, MCs, and other $P2Y_{12}$ receptor-bearing cells relevant to the pathophysiology of atherosclerosis.

Example 6

Materials and Methods

Cell Culture

Cells from the LAD2 line (Kirshenbaum, A. S., et al. 2003. *Leukemia Res.* 27:677-682) isolated from the bone marrow of a patient with MC leukemia were cultured in STEMPRO 34™ (Invitrogen) supplemented with 2 mM L-Glutamine (Invitrogen), Pen-strep (100 IU/ml) (Invitrogen) and SCF (Endogen) (100 ng/ml). Cell culture medium was hemi-depleted every week with fresh medium and 100 ng/ml SCF. CHO cells were grown in DMEM/F-12 with 10% FBS and Pen-strep (100 IU/ml) (Invitrogen).

Animals

BALB/c mice lacking both CysLT1R and CysLT2R (Cysltr1/Cysltr2$^{-/-}$ mice) and their wild-type littermate controls were derived as described elsewhere (Maekawa, A., et al. (2008) *Proc. Natl. Acad. Sci. U.S.A.* 105:16695-16700). Mice lacking $P2Y_{12}$ receptors (p2ry12$^{-/-}$ mice) were derived as described elsewhere (Neiswandt, B., et al. 2000. *Blood.* 96:2520-2527) on a mixed C57BL/6-129 background and backcrossed for 10 generations with C57BL/6 mice. Wild-type BALB/c and C57BL/6 mice were purchased from Taconic.

Calcium Flux

LAD2 cells (0.5-1×10$^6$/sample) were washed and labeled with fura 2-AM for 30 min at 37° C. Cells were stimulated with the indicated concentrations of $LTC_4$, $LTD_4$, and $LTE_4$, and changes in intracellular calcium concentration were measured using excitation at 340 and 380 nm in a fluorescence spectrophotometer (Hitachi F-4500) (Paruchuri, S., et al. 2008. *J. Biol. Chem.* 283:16477-16487). The relative ratios of fluorescence emitted at 510 nm were recorded and displayed as a reflection of intracellular calcium concentration. In some experiments, cells were pre-incubated with the $CysLT_1R$ antagonist MK571 (1 μM) or with the $P2Y_{12}$ receptor antagonist 2-MesAMP (100 μM) for 5 minutes before the stimulation.

Real-Time Quantitative Polymerase Chain Reaction (qPCR)

The expression of $P2Y_{12}$ receptor mRNA was determined with real time PCR performed on an ABI PRISM 7700 Sequence detection system (Applied Biosystems). RNA was isolated with an RNAeasy minikit (Qiagen), and was treated with RNase-free DNase (Invitrogen) according to the manufacturer's protocol. cDNA was synthesized from 1 μg RNA with Superscript II RNase H-RT (Invitrogen). RT was performed using TaqMan RT reagents. Primers and FAM-labeled PCR mix were purchased from Superarray.

Short Hairpin RNA (shRNA) Knock-Downs shRNA constructs targeting human $CysLT_1R$ and $P2Y_{12}$ receptors were purchased from Open Biosystems. The constructs were cloned into a lentiviral vector (pLKo1, Open Biosystems) and used to generate infectious particles with a lenitiviral packaging mix (Virapower, Invitrogen) according to the manufacturer's protocol. The transfections were carried out as described previously (Jiang, Y., et al. 2007. *Blood.* 110:3263-3270). FACs analysis was used to confirm the knock-downs of $CysLT_1R$, while qPCR was used to verify the knockdown of the $P2Y_{12}$ receptor.

Generation of Stable P2Y$_{12}$ Receptor Transfectants

A human P2Y$_{12}$ receptor cDNA was amplified by 30 cycles of PCR from reverse-transcribed total RNA extracted from primary cord blood hMCs. The primer sequences were 5'-CAACAAGAAATGCAAGCCGTCGA (SEQ ID NO: 1) and 3'-ACATTGGAGTCTCTTCATTTGG (SEQ ID NO: 2). The fragment was cloned into a TA vector (INVITROGEN™). After verifying the nucleotide sequence, the fragment was subcloned into the multiple cloning site of the expression vector pEF1/His B, encoding a C-terminal polyhistidine (HIS) tag. A plasmid expressing the P2Y$_{12}$ receptor construct in the forward orientation were transfected into CHO cells using Fugene HD reagent according to manufacturer's protocol. A construct in the reverse sequence was transfected in parallel as a negative control. Stably-expressing clones were selected in the medium containing 1000 μg/ml G418 (INVITROGEN™), and expression of the construct was confirmed by FACs analysis of permeabilized cells using a monoclonal Ab against the histidine tag.

Cell Activation

LAD2 cells were stimulated with the indicated concentrations of LTD$_4$ or LTE$_4$ or were passively sensitized with human myeloma IgE (2 μg/ml; Chemicon international) overnight and stimulated with rabbit anti-human anti-IgE (CHEMICON™, 1 μg/ml) as detailed elsewhere (Paruchuri, S., et al. 2008. J. Biol. Chem. 283:16477-16487). The concentration of MIP-1β was measured by an ELISA (ENDOGEN®). PGD$_2$ was quantitated by a PGD$_2$-methoxylamine hydrochloride (PGD$_2$-MOX) assay.

SDS PAGE Immunoblotting

After stimulation with the respective agonists, LAD2 cells and hMCs (0.5×10$^6$) were lysed with lysis buffer (BD Bioscience) supplemented with protease inhibitor cocktail (Roche) and sodium vanadate (1 mM). Lysates were subjected to 4-12% SDS-PAGE and transferred to PVDF membranes. The membranes were incubated with Abs against phospho and total ERK, MEK, 90 kDa ribosomal s6 kinase (p90RSK) and cyclic AMP regulated binding protein (CREB) (CELL SIGNALING TECHNOLOGIES®) in 1×PBS, 5% dry milk, 0.1% Tween-20 (1:1000) overnight at 4° C. on shaker, and then with secondary Ab (peroxidase-conjugated anti-rabbit or anti-mouse). Bands were visualized using enhanced chemiluminescence (Pierce).

Binding Assays

[$^3$H] LTD$_4$ was converted to [$^3$H]LTE$_4$ by the di-peptidases present in the serum. Briefly, 100 μl (80 nM) [$^3$H]LTD$_4$ was incubated with 100 μl of 10% serum for 2 h at room temperature. The converted product was extracted into 400 μl of methanol, evaporated in presence of nitrogen and diluted to the required concentration with the binding buffer for the binding assay. The conversion was confirmed by running an aliquot on high-performance reverse phase liquid chromatography. The fraction eluting with the LTE$_4$ peak accounted for >99% of the radioactivity used in the assays. [$^3$H]ADP and [$^3$H]LTE$_4$ binding assays were performed using membrane proteins as described previously (Maekawa, A., et al. (2001) Proc. Natl. Acad. Sci. U.S.A. 98:2256-2261). Briefly, cells were washed in PBS, resuspended in PBS supplemented with protease inhibitor cocktail and lysed by sonication for 5 min. The lysed cells were centrifuged at 100,000 Xg for 45 min and the microsomal pellet was resuspended in 1 ml PBS. Protein concentration was determined using Biorad Protein Assay Kit. 50 μg of membrane protein was incubated for 1 h at room temperature in 250 μl of 10 mM Hepes/KOH, pH 7.4, with various concentrations of radiolabeled ligand and cold competitor. Bound [$^3$H] was separated from free [$^3$H] by filtration through GF/C filters (Whatman) and washed twice with 10 mM Hepes/KOH, pH 7.4, containing 0.01% BSA. The residual membrane-associated [$^3$H] on the filter was determined in 2 ml scintillation fluid by beta counter (Perkin Elmer). For [$^3$H]ADP, specific binding was determined by subtracting the amount of [$^3$H] bound in the presence of 100 μM 2-MesADP from total binding. For [$^3$H]LTE$_4$, nonspecific binding was calculated as the residual radioactivity bound in the presence of unlabeled LTE$_4$ (10 μM).

Induction of Pulmonary Inflammation

Male BALB/c mice (6-8 weeks old) received intraperitoneal injections of reagent-grade chicken egg ovalbumin (OVA) (10 μg) precipitated with aluminum hydroxide (2.25 μg) on days 0 and 7. On days 13-15, the mice received single intranasal doses of LTD$_4$, LTE$_4$, or buffer. Twelve hours after each dose, the mice were exposed to an aerosol of 0.1% OVA for 30 min delivered by an ultrasonic nebulizer. As a positive control group, some mice received 1% OVA without LTD$_4$ or LTE$_4$ pre-treatment. The mice were euthanized 24 hours after their third and final aerosol challenge. In some experiments, the mice received clopidogrel (500 μg/ml) in drinking water for 3 days before receiving the first intranasal dose of LTs. The treatment was continued throughout the procedure.

For Der f-mediated pulmonary inflammation, 6-8 week old C57BL/6 mice were lightly anaesthetized and received either 3 or 10 μg of Der f extract (Greer Labs) on days 0, 3, 7, 10, 14 and 17. Some mice received clopidogrel throughout the duration of the experiment. Mice were euthanized 24 h after the last intranasal instillation.

Platelet Depletion

Sensitized mice were treated intravenously with 50 μg (~2 μg/g body weight) of a monoclonal rat IgG directed against mouse CD42b (GPIbα) or an equal amount of isotype control (both from Cemfret analytics). Each Ab was diluted in 50 μl of sterile saline. The depletion of platelets was confirmed by automated counting.

Histologic Assessment

The left lungs were fixed for at least 8 h in 4% paraformaldehyde and embedded in glycolmethacrylate, as described previously (Kim, D. C., et al. 2006. J. Immunol. 176:4440-4448). 2.5 μm thick glycolmethacrylate sections were stained with H&E for general morphologic examination. For histological study of the mucus-secreting cells of the epithelium (goblet cells) of the airways, lung sections were stained with Periodic acid-Shiff (PAS). The extent of cellular infiltration in the bronchovascular bundles was evaluated without knowledge of the particular treatment and was categorized arbitrarily as grade 0=no inflammation, grade 1=mild inflammation, grade 2=moderate inflammation, grade 3=severe inflammation. 15 bronchovascular bundles of each mouse were evaluated. The stained goblet cells were numerated in at least four independent bronchovascular bundles from the lung sections obtained for each animal in the different experimental groups. The length of basal lamina of corresponding bronchus was measured by Image J (NIH image analysis software). Only the comparable large-calibre, preterminal bronchi (diameter 200-220 um) were examined, since minimal changes occur in terminal bronchioles. The data were expressed as the average of goblet cell counts stained in each bronchus in each section per mm bronchial basal lamina.

Statistics

Data are expressed as mean±SD from at least three experiments except where otherwise indicated. Data were converted to a percentage of control for each experiment where indicated. Significance was determined with the Welch's test for samples of unequal variance. Analysis of variance was used to test differences between multiple groups.

The invention claimed is:

1. A method of treating aspirin-exacerbated respiratory disease (AERD) in a subject, the method comprising administering to a subject having AERD a therapeutically effective amount of a compound having the formula:

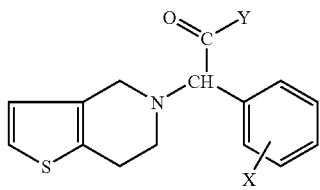

in which Y represent hydroxyl, an OR group wherein R is a straight or branched lower aklyl radical, or

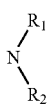

in which $R_1$ and $R_2$ are each independent of each other and represent hydrogen or a straight or branched lower alkyl group; or $R_1$ and $R_2$ form together with the nitrogen atom to which they are attached a heterocycle, selected from the group consisting of pyrrolidino, pipieridino, morpholino, piperazino, N-lower alkyl piperazino; and X represents hydrogen, a halogen or a lower alkyl radical; and their addition salts with pharmaceutically acceptable mineral or organic acids if Y represents the group OR or

or with mineral bases if Y represents OH, including both enantiomeric forms or their mixture.

2. The method of claim 1, wherein said compound comprises a dextro-rotatory enantiomer of the formula:

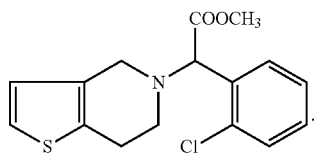

3. A method for treating aspirin-exacerbated respiratory disease (AERD) in a subject, the method comprising administering to a subject having AERD a compound selected from the group consisting of dextro-rotatory isomer of methyl alpha-5(4,5,6,7-tetrahydro(3,2-c)thieno pyridyl) (2-chlorophenyl)-acetate substantially separated from the levorotatory isomer and its pharmaceutically acceptable salts, hydrochloride of the dextro-rotatory isomer of methyl alpha-5(4,5,6,7-tetrahydro(3,2-c)thieno pyridyl) (2-chlorophenyl)-acetate substantially separated from the levo-rotatory isomer, hydrogen sulfate of the dextro-rotatory isomer of methyl alpha-5(4,5,6,7-tetrahydro(3,2-c)thieno pyridyl) (2-chlorophenyl)-acetate substantially separated from the levo-rotatory isomer, hydrobromide of the dextro-rotatory isomer of methyl alpha-5(4,5,6,7-tetrahydro(3,2-c)thieno pyridyl) (2-chlorophenyl)-acetate substantially separated from the levo-rotatory isomer, and taurocholate of the dextro-rotatory isomer of methyl alpha-5(4,5,6,7-tetrahydro(3,2-c)thieno pyridyl) (2-chlorophenyl)-acetate substantially separated from the levo-rotatory isomer.

4. The method of claim 1, wherein the subject has high urinary levels of $LTE_4$.

5. The method of claim 1, wherein the subject has selective hyperresponsiveness to $LTE_4$.

6. The method of claim 1, wherein the subject has asthma, nasal polyposis and/or marked cysteinal leukotriene (cys-LT) over-production.

* * * * *

UNITED STATES PATENT AND TRADEMARK OFFICE
CERTIFICATE OF CORRECTION

PATENT NO.        : 8,299,097 B2
APPLICATION NO.   : 12/557024
DATED             : October 30, 2012
INVENTOR(S)       : Joshua A. Boyce It is certified that error appears in the above-identified patent and that said Letters Patent is hereby corrected as shown below:

Col. 1, line 15

Replace "Grant No. AI53202 awarded by the National Institutes of"
with -- Grant Nos. AI053202 and AI078908 awarded by the National Institutes of --

Signed and Sealed this
Twenty-second Day of January, 2013

David J. Kappos
*Director of the United States Patent and Trademark Office*